United States Patent [19]
Cook et al.

[11] Patent Number: 5,698,391
[45] Date of Patent: *Dec. 16, 1997

[54] METHODS FOR SYNTHETIC UNRANDOMIZATION OF OLIGOMER FRAGMENTS

[75] Inventors: Phillip Dan Cook, San Marcos; David J. Ecker, Leucadia; Jacqueline Wyatt, Carlsbad; Thomas W. Bruice, Carlsbad; Kevin Anderson, Carlsbad; Ronnie Hanecak, San Clemente; Timothy Vickers, Oceanside; Peter Davis, Carlsbad; Susan M. Freier, San Diego; Yogesh S. Sanghvi, San Marcos; Vickie Brown-Driver, San Diego, all of Calif.

[73] Assignee: ISIS Pharmaceuticals, Inc., Carlsbad, Calif.

[*] Notice: The portion of the term of this patent subsequent to Feb. 22, 2014, has been disclaimed.

[21] Appl. No.: 357,396

[22] Filed: Dec. 16, 1994

Related U.S. Application Data

[63] Continuation-in-part of Ser. No. 196,103, Feb. 22, 1994, which is a continuation-in-part of Ser. No. 749,000, Aug. 23, 1991, abandoned.

[51] Int. Cl.$^6$ .................... C12Q 1/68; C12Q 1/70
[52] U.S. Cl. ........................................ 435/5; 435/6
[58] Field of Search ................................ 435/5, 6

[56] References Cited

U.S. PATENT DOCUMENTS

| | | | |
|---|---|---|---|
| 4,833,092 | 5/1989 | Geysen | 436/501 |
| 5,010,175 | 4/1991 | Rutter et al. | 530/334 |
| 5,194,392 | 3/1993 | Geysen | 436/578 |

FOREIGN PATENT DOCUMENTS

| | | |
|---|---|---|
| WO 86/00991 | 2/1986 | WIPO. |
| WO 92/19732 | 11/1992 | WIPO. |

OTHER PUBLICATIONS

Riordan et al., "Oligonucleotide-based therapeutics" Nature 350: 442-443, Apr. 1991.
Carell, T. et al., "A Solution-Phase Screening Procedure for the Isolation of Active Compounds form a Library of Molecules", Angew. Chem. Int. Ed. Engl. 1994, 33(20), 2061-2064.
Bock et al., "Selection of Single-Stranded DNA Molecules That Bind and Inhibit Human Thrombin," Nature 355: 564-566 (1992).
Buckheit et al., "Thiazolobenzimidazole: biological and biochemical anti-retroviral activity of a new nonnucleoside reverse transcriptase inhibitor," Antiviral Res. 21: 247-265 (1993).
Dooley et al., "Acetalins: Opioid receptor antagonists determined through the use of synthetic peptide combinatorial libraries," Proc. Nat'l Acad. Sci. U.S.A. 90: 10811-10815 (1993).

Dooley and Houghten, "The Use of Positional Scanning Synthetic Peptide Combinatorial Libraries for the Rapid Determination of Opioid Receptor Ligands," Life Sciences 52: 1509-1517 (1993).
Eichler and Houghten, "Identification of Substrate-Analog Trypsin Inhibitors through the Screening of Synthetic Peptide Combinatorial Libraries," Biochemistry 32: 11035-11041 (1993).
Ellington and Szostak, "In vitro selection of RNA molecules that bind specific ligands," Nature 346: 818-822 (1990).
Fodor et al., "Light-Directed, Spatially Addressable Parallel Chemical Synthesis," Science 251: 767-773 (1991).
Gallop et al., "Applications of Combinatorial Technologies to Drug Discovery 1. Background and Peptide Combinatorial Libraries," J. Med Chem. 37: 1233-1251 (1994).
Geysen et al., "A Priori of a Peptide Which Mimics a Discontinuous Antigenic Determinant," Molecular Immunology 23: 709-715 (1986).
Gordon et al., "Applications of Combinatorial Technologies to Drug Discovery 2. Combinatorial Organic Synthesis, Library Screening Strategies, and Future Directions," J. Med. Chem. 37: 1385-1401 (1994).
Houghten et al., "The Use of Synthetic Peptide Combinatorial Libraries for the Identification of Bioactive Peptides," BioTechniques 13: 412-421 (1992).
Houghten et al., "Generation and Use of Synthetic Peptide Combinatorial Libraries for Basic Research adn Drug Discovery," Nature 354: 84-86 (1991).
Jayawickreme et al., "Creation and functional screening of a multi-use peptide library," Proc. Natl. Acad. Sci. U.S.A. 91: 1614-1618 (1994).
Kramer et al., "Simultaneous Synthesis of Peptide Libraries on Single Resin and Continuous Cellulose Membrane Supports: Examples for the Identification of Protein, Metal and DNA Binding Peptide Mixtures," Peptide Res. 6: 314-319 (1993).
Lam et al., "A new type of synthetic peptide library for identifying ligand-binding activity," Nature 354: 82-84 (1991).
Needels et al., "Generation and screening of an olignucleotide-encoded synthetic peptide library," Proc. Natl. Acad. Sci. U.S.A. 90: 10700-10704 (1993).

(List continued on next page.)

Primary Examiner—Jasemine C. Chambers
Assistant Examiner—Scott D. Priebe
Attorney, Agent, or Firm—Woodcock Washburn Kurtz Mackiewicz & Norris, LLP

[57] ABSTRACT

Methods useful for the determination of oligomers which have specific activity for a target molecule from a pool of primarily randomly assembled oligomers are provided. The disclosed methods involve repeated syntheses of increasingly simplified sets of oligomers coupled with selection procedures for determining oligomers having the highest activity. Freedom from the use of enzymes allows the application of these methods to any molecules which can be oligomerized in a controlled fashion.

80 Claims, 7 Drawing Sheets

OTHER PUBLICATIONS

Owens et al., "The Rapid Identification of HIV Protease Inhibitors Through the Synthesis and Screening of Defined Peptide Mixtures," *Biochem. Biophys. Res. Commun.* 181: 402–408 (1991).

Pinilla et al., "Rapid Identification of High Affinity Peptide Ligands Using Positional Scanning Synthetic Peptide Combinatorial Libraries," *BioTechniques* 13: 901–905 (1992).

Tuerk and Gold, "Systematic Evolution of Ligands by Exponential Enrichment: RNA Ligands to Bacteriophage T4 DNA Polymerase," *Science* 249: 505–510 (1990).

Vickers et al., "Inhibition of HIV–LTR Gene Expression by Oligonucleotides Targeted of the TAR Element," *N.A.R.* 19: 3359–3368 (1991).

Van Der Zee et al., "Efficient Mapping and Characterization of a T Cell Epitope by the Simultaneous Synthesis of Multiple Peptides," *Euro. J. Immunol.* 19: 43–47 (1989).

Green et al., "In Vitro Genetic Analysis of the Tetrahymena Self–Splicing Intron," *Nature* 347: 406–408 (1990).

Robertson and Joyce, "Selection In Vitro of an RNA Enzyme that Specifically Cleaves Single–Stranded DNA," *Nature* 344: 467–468 (1990).

Joyce, "Amplification, Mutation and Selection of Catalytic RNA," *Gene* 82: 83–87 (1989).

Thiesen and Bach, "Target Detection Assay (TDA): A Versatile Procedure to determine DNA Binding Sites as Demonstrated on SP1 Protein," *Nucleic Acid Research* 18: 3203–3209 (1990).

Kinzler and Vogelstein, "The GLI Gene Encodes a Nuclear Protein Which Binds Specific Sequences in the Human Genome," *Molec. Cel. Biol.* 10: 634–642 (1990).

Kinzler and Vogelstein, "Whole Genome PCR: Application to the Identification of Sequences Bound by Gene Regulatory Proteins," *Nucleic Acid Research* 18: 3203–3209 (1989).

Blackwell et al., "Sequence–Specific DNA Binding by the c–Myc Protein," *Science* 250: 1149–1151 (1990).

Blackwell and Weintraub, "Differences and Similarities in DNA–Binding Preferences of MyoD and E2A Protein Complexes Revealed by Binding Site Selection," *Science* 250: 1104–1110 (1990).

Ecker et al., "Rational Screening of Oligonucleotide Combinatorial Libraries for Drug Discovery," *Nuc. Acids Res.* 21: 1853–1856 (1993).

Wyatt et al., "Combinatorially selected guanosine–quartet structure is a potent inhibitor of human immunodeficiency virus envelope–mediated cell fusion," *Proc. Nat'l Sci. USA* 91: 1356–1360 (1994).

Zuckerman et al., "Identification of highest–affinity ligands by affinity selection from equimolar peptide mixtures generated by robotic synthesis," *Proc. Nat'l Sci. USA* 89: 4505–4509 (1992).

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

GGUGGUGGUG GGCGCCGUCG GUGUGGGCAA GAGUGCGCUG ACCAUCC     47

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: misc_feature

```
            ( B ) LOCATION: 4
            ( D ) OTHER INFORMATION: /note="pyrene analog of adenine"

( x i ) SEQUENCE DESCRIPTION: SEQ ID NO:2:
```

NNNANGNNNN                                                                                          10

( 2 ) INFORMATION FOR SEQ ID NO:3:

```
    ( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( i i ) MOLECULE TYPE: RNA (genomic)

( i x ) FEATURE:
            ( A ) NAME/KEY: misc_feature
            ( B ) LOCATION: 4
            ( D ) OTHER INFORMATION: /note="pyrene analog of adenine"

( x i ) SEQUENCE DESCRIPTION: SEQ ID NO:3:
```

NNNANANNNN                                                                                          10

( 2 ) INFORMATION FOR SEQ ID NO:4:

```
    ( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( i i ) MOLECULE TYPE: RNA (genomic)

( i x ) FEATURE:
            ( A ) NAME/KEY: misc_feature
            ( B ) LOCATION: 4
            ( D ) OTHER INFORMATION: /note="pyrene analog of adenine"

( x i ) SEQUENCE DESCRIPTION: SEQ ID NO:4:
```

NNNANCNNNN                                                                                          10

( 2 ) INFORMATION FOR SEQ ID NO:5:

```
    ( i ) SEQUENCE CHARACTERISTICS:
            ( A ) LENGTH: 10 base pairs
            ( B ) TYPE: nucleic acid
            ( C ) STRANDEDNESS: single
            ( D ) TOPOLOGY: linear ( i i ) MOLECULE TYPE: RNA (genomic)

( i x ) FEATURE:
            ( A ) NAME/KEY: misc_feature
            ( B ) LOCATION: 4
            ( D ) OTHER INFORMATION: /note="pyrene analog of adenine"

( x i ) SEQUENCE DESCRIPTION: SEQ ID NO:5:
```

NNNANUNNNN                                                                                          10

( 2 ) INFORMATION FOR SEQ ID NO:6:

```
    ( i ) SEQUENCE CHARACTERISTICS:
            ( A ) LENGTH: 11 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO:6:
```

CCCUUCCANU C  11

(2) INFORMATION FOR SEQ ID NO:7:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:7:

CCCUUCCGNU C  11

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:8:

CCCUUCCCNU C  11

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:9:

CCCUUCCUNU C  11

(2) INFORMATION FOR SEQ ID NO:10:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:10:

CCCUUCCCAU C  11

(2) INFORMATION FOR SEQ ID NO:11:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:11:

CCCUUCCCGU C  11

(2) INFORMATION FOR SEQ ID NO:12:

( i ) SEQUENCE CHARACTERISTICS:
　　　　( A ) LENGTH: 11 base pairs
　　　　( B ) TYPE: nucleic acid
　　　　( C ) STRANDEDNESS: single
　　　　( D ) TOPOLOGY: linear ( i i ) MOLECULE TYPE: RNA (genomic)

( x i ) SEQUENCE DESCRIPTION: SEQ ID NO:12:

CCCUUCCCCU C    11

( 2 ) INFORMATION FOR SEQ ID NO:13:

( i ) SEQUENCE CHARACTERISTICS:
　　　　　　( A ) LENGTH: 11 base pairs
　　　　　　( B ) TYPE: nucleic acid
　　　　　　( C ) STRANDEDNESS: single
　　　　　　( D ) TOPOLOGY: linear ( i i ) MOLECULE TYPE: RNA (genomic)

( x i ) SEQUENCE DESCRIPTION: SEQ ID NO:13:

CCCUUCCCUU C    11

( 2 ) INFORMATION FOR SEQ ID NO:14:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( i i ) MOLECULE TYPE: RNA (genomic)

( x i ) SEQUENCE DESCRIPTION: SEQ ID NO:14:

GCGNNNANNN NNCGC    15

( 2 ) INFORMATION FOR SEQ ID NO:15:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( i i ) MOLECULE TYPE: RNA (genomic)

( x i ) SEQUENCE DESCRIPTION: SEQ ID NO:15:

GCGNNNGNNN NNCGC    15

( 2 ) INFORMATION FOR SEQ ID NO:16:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( i i ) MOLECULE TYPE: RNA (genomic)

( x i ) SEQUENCE DESCRIPTION: SEQ ID NO:16:

GCGNNNCNNN NNCGC    15

( 2 ) INFORMATION FOR SEQ ID NO:17:

( i ) SEQUENCE CHARACTERISTICS:
　　　　　　( A ) LENGTH: 15 base pairs
　　　　　　( B ) TYPE: nucleic acid
　　　　　　( C ) STRANDEDNESS: single
　　　　　　( D ) TOPOLOGY: linear ( i i ) MOLECULE TYPE: RNA (genomic)

( x i ) SEQUENCE DESCRIPTION: SEQ ID NO:17:

GCGNNNUNNN NNCGC 15

( 2 ) INFORMATION FOR SEQ ID NO:18:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

AAGACGTCTT GCG 13

( 2 ) INFORMATION FOR SEQ ID NO:19:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

TCTGCAGAAC GC 12

( 2 ) INFORMATION FOR SEQ ID NO:20:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:20:

GCCAGAUCUG AGCCUGGGAG CUCUCUGGC 29

( 2 ) INFORMATION FOR SEQ ID NO:21:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:21:

CUGGCCUUCC UACAAGGGAA GGCCAG 26

METHODS FOR SYNTHETIC UNRANDOMIZATION OF OLIGOMER FRAGMENTS

CROSS REFERENCE TO RELATED APPLICATIONS

This application is a continuation-in-part of U.S. Ser. No. 196,103 filed Feb. 22, 1994 which is a continuation-in-part of U.S. Ser. No. 749,000 filed Aug. 23, 1991 now abandoned, entitled "Synthetic Unrandomization of Oligomer Fragments" and assigned to the assignee of the present application. The entire disclosure of these applications is incorporated by reference herein.

FIELD OF THE INVENTION

This invention relates to the development of drugs and of biologically active diagnostics and research reagents. In particular, this invention relates to the synthetic unrandomization of oligomers to determine oligomers having a desired target property.

BACKGROUND OF THE INVENTION

Oligomers may be designed which are useful for therapeutic, diagnostic and research applications. In the past, development of biologically active oligomer substances was often limited to the modification of known sequences, unit by unit, until a desired characteristic or efficacy was achieved. However, in addition to time drawbacks, protocols employing these types of methodologies are limiting in that the final product is based upon, and often not far removed from, the structure of the starting material.

Recently, new methods have been developed whereby drugs and biologically active substances can be "designed." One such method that can be used for the rapid identification of active molecules is positional scanning. Pinilla et al., *BioTechniques* 1992, 13, 901; Dooley and Houghten, *Life Sciences* 1993, 52, 1509; and Houghten et al., *BioTechniques* 1992, 13, 412. Subsets of oligomers are prepared, in each of which a common position of the oligomer is defined by each of the monomer units being used. As a result, each subset represents a different monomer unit at an identical defined position. The remaining positions in the oligomers of each subset are randomized. The number of subsets prepared is proportional to the number of monomer units being used. This process is repeated with additional subsets (for each of the positions in the oligomer) wherein each subsequent subset has a common position which is distinct from that of an earlier subset, and the remaining positions in the oligomers are randomized. The most active oligomer from each subset reveals the best monomer unit for each of the defined positions of the oligomer. The cumulative results from all the subsets is useful in identifying the "winner," which is the oligomer with best specific activity.

Combinatorial strategies are useful for the identification of active peptides. Geysen (U.S. Pat. No. 5,194,392 issued Mar. 16, 1993) discloses a method of detecting or determining a sequence of monomers which is topologically equivalent to an epitope of an antigen which is complementary to a particular paratope of an antibody of interest. The method of Geysen requires that at least two positions on the polypeptide catamer be fixed in order to detect even minimal activity. Geysen's method further requires that the target antibody of interest be a known, isolated species.

A variety of other combinatorial strategies have been described to identify active peptides. Houghten et al., *Nature* 1991, 354, 84; Lam et al., *Nature* 1991, 354, 82; Owens et al., *Biochem. Biophys. Res. Commun.* 1991, 181, 402; Fodor et al., *Science* 1991, 251, 767; Geysen et al., *Molecular Immunology* 1986, 23, 709; Zuckermann et al., *Proc. Natl. Acad. Sci.* 1992, 89, 4505; Rutter et al., U.S. Pat. No. 5,010,175 issued Apr. 23, 1991; Needels et al., *Proc. Natl. Acad. Sci. U.S.A.* 1993, 90, 10700; Eichler and Houghten, *Biochemistry* 1993, 32, 11035; Dooley et al., *Proc. Natl. Acad. Sci. U.S.A.* 1993, 90, 10811; Dooley and Houghten, *Life Sciences* 1993, 52, 1509; Jayawickreme et al., *Proc. Natl. Acad. Sci. U.S.A.* 1994, 91, 1614; Gallop et al., *J. Med. Chem.* 1994, 37, 1233; Gordon et al., *J. Med. Chem.* 1994, 37, 1385; and Kramer et al., *Peptide Res.* 1993, 6, 314.

Combinatorial nucleic acid selection methods have been generally used to select specific nucleic acid sequences from a pool of random nucleic acid sequences based on the ability of selected sequences to bind to a target protein. The selected sequences are then commonly amplified and the selection process repeated until a few strong binding sequences are identified. These methods generally employ enzymatic steps within the protocol. Commonly T7 RNA polymerase and Taq I associated with polymerase chain reaction amplification methods are employed. One group has identified a target sequence to the RNA-binding protein gp43. Tuerk and Gold, *Science* 1990, 249, 505. The method of Tuerk and Gold, referred to as "systematic evolution of ligands by exponential enrichment" (SELEX), identified specifically bindable RNA sequences using four cycles of amplification of RNA sequences having variable portions therein and which were specifically bindable to gp43.

Another group designed DNA molecules which recognized the protease thrombin. Bock et al., *Nature* 1992, 355, 564. This method involves the preparation of a population involving a random region flanked by known primer regions followed by PCR amplification and selection. Small molecule mimics of metabolic cofactors have been selectively recognized by RNA sequences in this manner by Ellington and Szostak, *Nature* 1990, 346, 818. These techniques were suggested to be useful in designing oligonucleotide ligands. However, their dependence upon enzymatic means for amplification and sequence determination limits their utility. Simpler methods for the identification of useful oligomers which have desired target properties such as oligomers which bind with specificity to target molecules and/or which have catalytic, enzymatic, or inhibitory activity are greatly desired. In particular, viral inhibition properties are also target properties of interest. Methods which are not dependent upon enzymatic means for amplification and resolution of oligonucleotides of interest would simplify protocols as well as expand the range of substrates with which the protocols would be effective. For example, presently there are over one hundred nucleotide analogs available. Cook, *Anti-Cancer Drug Design* 1991, 6, 585; and Uhlmann et al., *Chem. Rev.* 1990, 90, 544. Since not all analogs are amenable to enzymatic processes, a non-enzymatic means for determining useful oligomer sequences which have desired target properties is greatly desired. For example, such methods could determine oligomers which bind specifically, not only to natural nucleic acid-binding proteins, but also to any protein, nucleic acid, or other target molecule. Further, such methods could determine oligomers which inhibit viral proliferation without the need to have prior knowledge of the viral target or oligomer sequence.

BRIEF DESCRIPTION OF THE DRAWINGS

FIG. 1 is a schematic representation of the nucleotide sequence and secondary structure of the ras 47-base-pair stem/loop (SEQ ID NO:1) RNA.

SUMMARY OF THE INVENTION

Figure 2A:
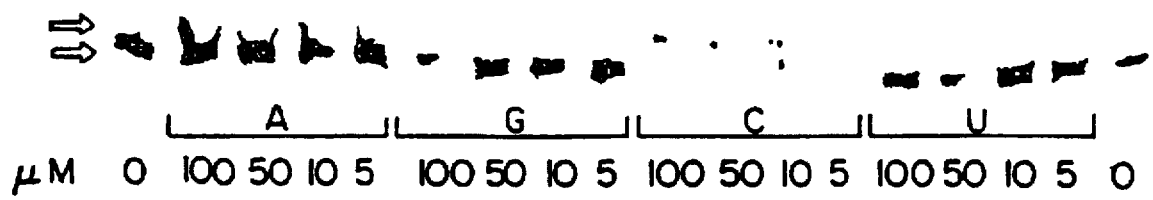
FIGS. 2A, 2B and 2C are represenation of gel images of a gel shift assay showing binding affinity of RNA oligonucleotides with ras 47-base-pair stem/loop RNA.

Combinatorial synthetic strategies offer the potential to generate and screen extremely large numbers of compounds and identify individual molecules with desired binding affinity or specific activity. This invention is directed to substantially non-enzymatic methods of determining oligomers which have a desired target activity. Such oligomers preferably exhibit desired activity, such as inhibitory, catalytic or enzymatic activity which activity generally involves binding by the oligomer to a target molecule which may or may not be previously known.

Methods of the present invention are useful for the determination of oligomers, which have specific target activity from a pool of primarily randomly assembled oligomers. Said methods involve iterative syntheses of increasingly simplified sets of oligomers coupled with selection procedures for determining the oligomer set having the greatest specific activity, in an assay for desired activity such as against a given target molecule.

Simplification of the pool occurs because, with each additional step of the method, at least one additional position in the oligomer is determined. As a result, the possible number of different oligomer molecules in the pool decreases sequentially with a decrease in the number of random positions remaining in the oligomer.

Freedom from the use of enzymes allows the application of these methods to any molecule which can be oligomerized in a controlled fashion. These methods may also be used for identifying active oligomers from a library of circular or cyclic oligomers.

In one embodiment of the present invention, methods for determining oligomers having specific target activity are provided. In preferred embodiments of the invention, the oligomers are oligonucleotides or macrocyclic amines. These methods involve preparing a group comprising a plurality of sets of oligomers, each oligomer comprising at least three monomer units, by defining a common position in the oligomers of the sets and synthesizing said sets of oligomers such that each set has a different monomer unit in said common position and the monomer units which are not in the common position are randomized. "Common position," in the context of this invention, refers to a monomer position in the oligomer that is kept fixed in all the oligomers sets, and comprises a known different monomer unit in each oligomer set. Each of the sets is then assayed for a desired target activity such as binding activity against the target molecule and the set having optimal target activity is selected.

In other embodiments of the present invention each group of oligomers may be subfractionated to provide subfractions of the sets of oligomers. Each subfraction may be assayed for target activity and the set from which the subfraction having optimal activity was derived, is selected.

These methods further comprise preparing a further group comprising a plurality of sets of oligomers, each of the sets having in the previously defined common position the monomer unit appearing in that position in the previously selected set. Each of said further group of sets has a different monomer unit in an additional defined common position. The monomer units in positions of the oligomers which are not in a common position are randomized. In other embodiments of the invention this group may be subfractionated to provide subfractions of the sets of oligomers.

Each of said sets or subfractions of sets may be assayed for target activity and the set having optimal activity, or the set from which the subfraction having the optimal activity was derived, is selected. The preceding steps may be performed iteratively.

Methods of determining an oligomer cassette having specific target activity are also provided by the present invention. These methods involve preparing a group comprising a plurality of sets of oligomers, each oligomer comprising at least three monomer units, by defining a common position in the oligomers of the sets and synthesizing said sets of oligomers such that each set has a different monomer unit in said common position and the monomer units which are not in the common position are randomized. Each of the sets are then assayed for target activity and the set having optimal activity is selected. Thereafter, a further group is prepared comprising a plurality of sets of oligomers, each of the sets having in that position the monomer unit appearing in the previously defined common position in the previously selected set. Each of said further group of sets has a different monomer unit in an additional defined common position. The monomer units in positions of the oligomers which are not in a defined common position are randomized. Each set of said further group is assayed for specific target activity and the set having optimal activity is selected. The preceding steps are performed iteratively to provide an oligomer cassette having each position defined.

In other embodiments of the invention, further methods for determining an oligomer having specific target activity are provided. Such methods comprise preparing a group comprising a plurality of sets of oligomers, each of which oligomers comprises at least one oligomer cassette and at least one flanking region. A common position is defined in a flanking region of the oligomers of the sets and the sets of oligomers are synthesized such that each set has a different monomer unit in said common position and the monomer units which are not in the common position are randomized. Each of the sets are then assayed for target activity and the set having optimal activity is selected.

These methods also may comprise preparing a further group comprising a plurality of sets of oligomers, each of the sets having in the previously defined common position the monomer unit appearing in that position in the previously selected set. Each of said further group of sets having a different monomer unit in an additional defined common position in the flanking region. The monomer units in positions of the oligomers which are not in a common position in the flanking region are randomized. Each of the sets of oligomers are assayed for specific target activity and the set having optimal activity is selected. The preceding steps may be and preferably are performed iteratively.

In some embodiments, the specific activity of the "winning" or chosen oligomer may be further improved by "mutation" of the chosen oligomer sequence, which comprises substitution of a single monomer unit within the "winner" with other monomer units. If this procedure results in the determination of an oligomer with improved activity, that oligomer sequence is then further modified by substitution of another single monomer unit with other monomers. The "winner" oligomer length may also be altered by the addition or deletion of at least one monomer unit. This is followed by determination target activity. This process may be repeated, preferably until no improvement in target activity of the oligomer is observed. Libraries of cyclic or circular oligomers are also amenable to improvement in specific target activity by this method.

In some embodiments of the present invention the complexity of a group of oligomers is decreased while optimizing the monomer composition of the oligomers. This method involves the identification of optimal monomers prior to the process of synthetic unrandomization. According to this embodiment, "subtractive" sets of completely random oligomers are prepared. A group of monomer units is selected and sets of randomized oligomers are synthesized. Each set is synthesized using all but at least one defined monomer unit from said group of selected monomer units, the excluded monomer or monomers being different in each set of randomer oligomers. The sets of oligomers are assayed for target activity and the sets of oligomers have little or no target activity are selected, whereby the monomer unit excluded from the selected set or sets is identified as being critical for the target activity of interest. This "subtractive" strategy may also be used for the determination of molecules with desired specific activity from a library of circular or cyclic oligomers.

In further embodiments of the present invention, monomer units of structure I are provided:

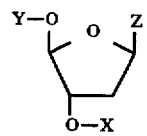

wherein:

X is H, a phosphate group, an activated phosphate group, an activated phosphite group, or a solid support;

Y is H, or a hydroxyl protecting group; and

Z is structure II:

Structure II wherein:

$R_1$ and $R_2$, together, form a five-membered heterocycle containing 1 to 3 nitrogen atoms, the remaining atoms are carbon atoms, being connected to the pentofuranosyl ring of structure I by one of the ring nitrogen atoms;

$V_1$ and $V_2$ are linked together and form a six-membered ring and are CH=CH—CH=CH, C(NH)—NH—NH—C(NH), C(O)—NH—NH—C(O), CH(NH$_2$)—NH—NH—C(O), C(O)—NH—NH—CH(NH$_2$), or CH(NH$_2$)—NH—NH—CH(NH$_2$); or $V_1$ and $V_2$ are, independently, C(O)—NH$_2$, or C(O)OV$_3$, where V$_3$ is alkyl having 1 to about 5 carbon atoms. Said monomer units may be incorporated into oligomers in still other embodiments of the present invention.

DETAILED DESCRIPTION OF THE INVENTION

The present invention, referred to as SURF™ (Synthetic Unrandomization of Random Fragments), is directed to non-enzymatic methods for determining oligomers which have specific target activity. Target activity is any activity which can be detected in a quantitative manner. Thus, in one embodiment of the present invention methods of determining oligomers having specific binding affinity for a target molecule are provided. Another embodiment of the present invention provides methods for determining oligomers having inhibitory activity or catalytic activity.

In the context of the present invention an oligomer is a string of monomer units linked together by covalent linkages. Oligomers of the present invention may be linear or cyclical as described by Blumenfeld, et al., WO 92/19732. Nucleic acids linked together via phosphodiester bonds and carbohydrates are examples of naturally occurring oligomers. Examples of rationally designed synthetic oligomers include compounds such as macrocyclic amines possessing several reactive centers, with varying degrees of reactivity and/or functional groups, for chemical manipulation and generation of cyclic combinatorial libraries.

In the context of this invention, the term "oligonucleotide" refers to a polynucleotide formed from naturally occurring bases and furanosyl groups joined by native phosphodiester bonds. This term effectively refers to naturally occurring species or synthetic species formed from naturally occurring subunits or their close homologs. The term "oligonucleotide" may also refer to moieties which have portions similar to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art. In accordance with some preferred embodiments, at least one of the phosphodiester bonds of the oligonucleotide has been substituted with a structure which functions to enhance the stability of the oligonucleotide or the ability of the oligonucleotide to penetrate the region of cells where the viral RNA is located. It is preferred that such substitutions comprise phosphorothioate bonds, phosphotriesters, methyl phosphonate bonds, short chain alkyl or cycloalkyl structures or short chain heteroatomic or heterocyclic structures. Most preferred are $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ structures. Also preferred are morpholino structures. Summerton and Weller, U.S. Pat. No. 5,034,506 issued Jul. 23, 1991. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen et al., Science 1991, 254, 1497. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the furanosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O-, S-, or N-alkyl; O-, S-, or N-alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Cook and Baschang, U.S. Pat. No. 5,359,044 issued Oct. 25, 1994. Oligonucleotides may also comprise other modifications consistent with the spirit of this invention. Such oligonucleotides are best described as being functionally interchangeable with yet structurally distinct from natural oligonucleotides. All such modifications are encompassed by this invention so long as they effectively function as subunits in the oligonucleotide. Oligonucleotides may be circular, as described by Blumenfeld et al., WO 92/19732.

In one embodiment of this invention, the oligomer comprises a plurality of monomer units joined together by alkylene glycol phosphate or hydroxy pyrrolidine phosphate linkages. These may include one or more monomers of structure III:

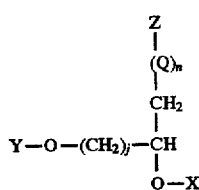

Structure III wherein:

X is H, a phosphate group, an activated phosphate group or an activated phosphite group;

Y is H or a hydroxyl protecting group;

E is O or S;

Z is $L_1$, $L_1$-$G_1$, $L_2$, $L_2$-$G_2$, $NR_3R_4$, a nitrogen-containing heterocycle, a phosphate group, a polyether group, or a polyethylene group;

$L_1$ is $C_1$-$C_{20}$ alkyl, $C_2$-$C_{20}$ alkenyl or $C_2$-$C_{20}$ alkynyl;

$L_2$ is $C_6$-$C_{14}$ aryl or $C_7$-$C_{15}$ aralkyl;

$G_1$ is halogen, $OR_1$, $SR_2$, $NR_3R_4$, C(=NH)$NR_3R_4$, NHC(=NH)$NR_3R_4$, CHO, C(=O)$OR_5$, CH($NR_3R_4$)(C(=O)$OR_5$), C(=O)$NR_3R_4$, a metal coordination group, or a phosphate group;

$G_2$ is halogen, OH, SH, $SCH_3$, or $NR_3R_4$;

$R_1$ is H, $C_1$-$C_6$ alkyl or a hydroxyl protecting group;

$R_2$ is H, $C_1$-$C_6$ alkyl or a thiol protecting group;

$R_3$ and $R_4$ are, independently, H, $C_1$-$C_6$ alkyl or an amine protecting group;

$R_5$ is H, $C_1$-$C_6$ alkyl or an acid protecting group;

Q is $L_1$, $G_3$, $L_1$-$G_3$, or $G_3$-$L_1$-$G_3$;

$G_3$ is $NR_3$, C(=O), C(=S), C(=O)—O, C(=O)—NH, C(=S)—O, C(=S)—NH, C(=S)—S (O)$_2$, $NR_3$C(=O), $NR_3$C(=S), $NR_3$C(=O)—O, $NR_3$C(=O)—NH, $NR_3$C(=S)—O, $NR_3$C(=S)—NH, or $NR_3S(O)_2$;

n is 0 or 1; and j is 1 to 6;

and/or structure IV:

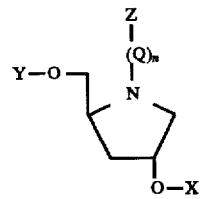

Structure IV wherein:

X is H, a phosphate group, an activated phosphate group or an activated phosphite group;

Y is H or a hydroxyl protecting group;

E is O or S;

Z is $L_1$, $L_1$-$G_1$, $L_2$, $L_2$-$G_2$, $NR_3R_4$, a nitrogen-containing heterocycle, a phosphate group, a polyether group, or a polyethylene group;

$L_1$ is $C_1$-$C_{20}$ alkyl, $C_2$-$C_{20}$ alkenyl or $C_2$-$C_{20}$ alkynyl;

$L_2$ is $C_6$-$C_{14}$ aryl or $C_7$-$C_{15}$ aralkyl;

$G_1$ is halogen, $OR_1$, $SR_2$, $NR_3R_4$, C(=NH)$NR_3R_4$, NHC(=NH)$NR_3R_4$, CHO, C(=O)$OR_5$, CH($NR_3R_4$) (C(=O)$OR_5$), C(=O)$NR_3R_4$, a metal coordination group, or a phosphate group;

$G_2$ is halogen, OH, SH, $SCH_3$, or $NR_3R_4$;

$R_1$ is H, $C_1$-$C_6$ alkyl or a hydroxyl protecting group;

$R_2$ is H, $C_1$-$C_6$ alkyl or a thiol protecting group;

$R_3$ and $R_4$ are, independently, H, $C_1$–$C_6$ alkyl or an amine protecting group;

$R_5$ is H, $C_1$–$C_6$ alkyl or an acid protecting group;

Q is $L_1$, $G_3$, $L_1$-$G_3$, or $G_3$-$L_1$-$G_3$;

$G_3$ is C(=O), C(=S), C(=O)—O, C(=O)—NH, C(=S)—O, C(=S)—NH, or C(=S)—S (O)$_2$; and n is 0 or 1.

The monomer units used in methods of the present invention may be appropriately functionalized and can be considered, for identification purposes, as substituted alkane glycols. The hydroxyl groups of the alkane glycols are used to link adjacent monomer units and may form oligomeric structures containing an alkylene glycol phosphate backbones. Similarly, monomer units of the invention may also be functionalized to contain a pyrrolidine moiety bearing a number of functional groups. Certain functional groups of the pyrrolidine monomer units may be linked to form oligomers with hydroxy pyrrolidine phosphate backbones.

Oligomers of the present invention may also include, but are not limited to, macrocyclic amines such as compounds having structure V:

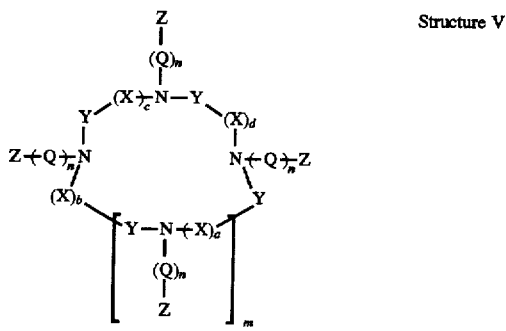

Structure V wherein:

X is $(CH_2)_a$ or O;

Y is $(CH_2)_b$ or O;

or X and Y, taken together complete an alicyclic or heterocylcic ring where a+b is less than or equal to 6;

Z is $L_1$, $L_1$-$G_1$, $L_2$, $L_2$-$G_2$, $NR_3R_4$, a nitrogen-containing heterocycle, a phosphate group, a polyether group, or a polyethylene group;

$L_1$ is $C_1$–$C_{20}$ alkyl having, $C_2$–$C_{20}$ alkenyl or $C_2$–$C_{20}$ alkynyl;

$L_2$ is $C_6$–$C_{14}$ aryl or $C_7$–$C_{15}$ aralkyl;

$G_1$ is halogen, $OR_1$, $SR_2$, $NR_3R_4$, C(=NH)$NR_3R_4$, NHC(=NH)$NR_3R_4$, CHO, C(=O)$OR_5$, CH($NR_3R_4$)(C(=O)$OR_5$), C(=O)$NR_3R_4$, a metal coordination group, or a phosphate group;

$G_2$ is halogen, OH, SH, $SCH_3$, or $NR_3R_4$;

$R_1$ is H, $C_1$–$C_6$ alkyl or a hydroxyl protecting group;

$R_2$ is H, $C_1$–$C_6$ alkyl or a thiol protecting group;

$R_3$ and $R_4$ are, independently, H, $C_1$–$C_6$ alkyl or an amine protecting group;

$R_5$ is H, $C_1$–$C_6$ alkyl or an acid protecting group;

Q is $L_1$, $G_3$, $L_1$-$G_3$, or $G_3$-$L_1$-$G_3$;

$G_3$ is C(=O), C(=S), C(=O)—O, C(=O)—NH, C(=S)—O, C(=S)—NH, or C(=S)—S(O)$_2$;

a, b, c and d are, independently 1 to about 10, preferably about 1 to about 3;

n is 0 or 1; and m is 0 to about 50, preferably about 1 to about 25.

The methods of the present invention are useful for determining oligomers which have a specific target activity.

In the context of the present invention, "determine" refers to concurrent or simultaneous identification of the sequence of an oligomer and the target activity of an oligomer. Target activity can be binding, inhibitory or catalytic activity. In some instances, neither the oligomer sequence nor its specific activity is known prior to performance of methods of the present invention. In other cases, while a particular oligomer sequence may be known, those skilled in the art may not recognize its activity for a particular target molecule. In still other cases, activity of a known sequence for a particular target molecule may be optimized.

Oligomers of the present invention are assayed for specific target activity. In some embodiments of the present invention, specific target activity refers to binding affinity of said oligomers for a target molecule. In other embodiments of the present invention, specific activity encompasses encompasses activity such as inhibitory or catalytic activity. As used herein, binding affinity refers to the ability of the oligomer to bind to a target molecule via hydrogen bonds, van der Waals interactions, hydrophobic interactions, or otherwise. For example, an oligonucleotide may have binding affinity for another oligonucleotide to which it is complementary, i.e., to which it has the ability to hybridize due to Watson-Crick base pair attraction.

Target molecules of the present invention may include any of a variety of biologically significant molecules. Target molecules may be nucleic acid strands such as significant regions of DNA or RNA. Target molecules may also include proteins, carbohydrates, nucleoproteins and/or glycoproteins. In some preferred embodiments of the present invention, said target molecule is a protein such as an immunoglobulin, receptor, receptor binding ligand, antigen or enzyme and more specifically may be a phospholipase, tumor necrosis factor, endotoxin, interleukin, plasminogen activator, protein kinase, cell adhesion molecule, lipoxygenase, hydroiase or transacylase. In other preferred embodiments of the present invention, said target molecules may be derived from a human immunodeficiency virus, Candida, a herpes virus, a papillomavirus, a cytomegalovirus, a rhinovirus, a hepatitis virus, or an influenza virus. In the context of this invention, "derived from" indicates the source of the target molecule; it is not necessary for the target molecule to be isolated or purified from the source from which it is derived. In still further preferred embodiments of the present invention, said target molecule is ras stem loop RNA, the TAR element of human immunodeficiency virus or the gag-pol stem loop of human immunodeficiency virus (HIV) or the HIV tat protein. Still other targets may induce cellular activity. For example, a target may induce interferon.

In the present invention, a group of sets of random oligomers is prepared. Oligomers may be prepared by procedures known to those skilled in the art including coupling via solution phase or solid phase chemistries. Representative solution phase techniques are described in U.S. Pat. No. 5,210,264 issued May 11, 1993. Representative solid phase techniques are those typically employed for DNA and RNA synthesis utilizing standard phosphoramidite chemistry. Protocols for Oligonucleotides and Analogs, S. Agrawal (Ed.), Humana Press, Totowa, N.J., 1993. A preferred solid phase synthesis utilizes phosphoramidites as activated phosphates. The phosphoramidites utilize $p^{III}$ chemistry. The intermediate phosphite compounds are subsequently oxidized to the $p^V$ state using known methods. This allows for the synthesis of the preferred phosphodiester or phosphorothioate linkages depending upon oxidation conditions selected. Other phosphate linkages can also be generated. These include phosphorodithioates, phosphotriesters, alkyl phosphonates, phosphoroselenates and phosphoramidates.

Further compounds of this invention include oligomers having at least one phosphodiester linkage and at least one phosphorothioate linkage.

In some embodiments of the present invention oligomer groups may further be labeled, such as by radiolabeling or fluorescent labeling. For example, an oligonucleotide group may be labeled at the 5' termini of the oligonucleotides using [γ-$^{32}$p] ATP and T4 polynucleotide kinase. Labeled oligomer groups may be useful in a number of assays which cannot be performed using unlabeled oligomer groups.

Oligomers of each set are generally of predetermined length. It is preferred that such oligomers be from about 3 to about 50 monomer units in length. It is also preferred for some embodiments of the present invention that less than about 10 monomer units of an oligomer are randomized.

In some embodiments of the present invention, the length of said oligomer need not be constant throughout the procedure. For example, an 8-mer may be assayed to determine the sequence having optimal activity. Subsequently, the 8-mer cassette may be extended and tested as a 15-mer to determine the 15-mer sequence having the optimal activity.

Groups of the present invention are made up of a plurality of sets which may remain constant throughout the procedure. The number of sets that make up each group is dependent upon the number of monomers units in the set. For example, an oligonucleotide group comprising naturally occurring nucleotides may be comprised of four sets since there are four naturally occurring bases that make up the nucleic acids, i.e. guanine, adenine, cytosine and thymine or adenine, guanine, cytosine and uracil. Alternatively, an oligonucleotide group may be comprised of more than four sets representing, for example, the four commonly occurring bases and additional modified bases. Of course, the number of monomer units which may be utilized in methods of the present invention is not limited and includes any monomer unit amenable to incorporation in a polymer. Subgroups of monomer units may also determine the number of sets in any one group. For example, in procedures to determine a particular polypeptide, sets may represent acidic, basic and neutral amino acid units, i.e. three sets. The number of sets in a group in any one procedure need not remain constant throughout, but may fluctuate. For example, in one group there may be three sets representing three types of polypeptides and in a next group there may be twenty sets representing each commonly occurring amino acid. Groups or libraries need not be limited to monomer units that belong to the same chemical class of compounds.

The use of additional monomer units may be preferred in some instances where it is desirable to increase the complexity of the group of oligomers. The complexity of a group may be calculated by the formula (P·P$^N$) where P is the number of different units used and N is the number of positions in an oligomer which are randomized. The complexity of a set (Q) is represented by the formula P$^N$. Table 1 illustrates the change in group complexity as a result of the increase in the number of analogs used. Of course, the number of different units used also determines the number of sets prepared.

TABLE 1

| Group Structure = NNN X NNN | | |
|---|---|---|
| Number of different analogs used (P) | Complexity of each set (Q) (P$^6$) | Total Group Complexity (P · P$^6$) |
| 4 | $4^6$ = 4096 | 4 × 4096 = 16,384 |
| 5 | $5^6$ = 15,625 | 5 × 15,625 = 78,125 |
| 6 | $6^6$ = 46,656 | 6 × 46,656 = 279,936 |
| 7 | $7^6$ = 117,649 | 7 × 117,649 = 823,543 |
| 8 | $8^6$ = 262,144 | 8 × 262,144 = 2,097,152 |

TABLE 1-continued

| Group Structure = NNN X NNN | | |
|---|---|---|
| Number of different analogs used (P) | Complexity of each set (Q) (P$^6$) | Total Group Complexity (P · P$^6$) |
| 9 | $9^6$ = 531,441 | 9 × 531,441 = 4,782,969 |
| 10 | $10^6$ = 1,000,000 | 10 × 1,000,000 = 10,000,000 |

Each of the sets in a group has a different monomer unit in a particular common position of said oligomer. For example, in determining an oligonucleotide comprising only naturally occurring bases, one of the four sets will contain adenine in the chosen common position, one set will contain guanine in the chosen common position, etc. The remaining positions in each set of oligonucleotides are comprised of random mixtures of monomer units.

In further embodiments of the present invention, common positions are comprised of multiple oligomer positions. For example, for a 9-mer, one common position may be the third position of the 9-mer, or the common position may be comprised of the third position and the fourth position of the 9-mer. It is not necessary that the oligomer be unrandomized from one end to the other. In some aspects of the invention, it may be preferable to begin a procedure by unrandomizing central regions of an oligomer as opposed to terminal positions.

Furthermore, there is a complexity limit to the detectability of activity (signal-to-noise), especially in oligomers having a high percentage of unrandomized positions. It is likely that with largely unstructured, conformationally dynamic oligomers, a plethora of molecules with relatively weak specific activity towards many target molecules will result. As discussed, this may be improved by increasing the number of units used. An additional method of increasing specific activity of a group of oligomers is to constrain the oligomer sterically. For example, an oligonucleotide may be sterically constrained by providing complementary ends at the 3' and 5' termini of the region of interest, which region comprises randomized positions. The complementary ends will hybridize to form a secondary structure.

The detectable specific activity may also be enhanced by the determination and/or use of an oligomer "cassette". An oligomer cassette is an oligomer for which a sequence has been determined, and is usually contained within a larger oligomer sequence. The cassette may comprise a sequence of known significance, or may be determined such as by the procedures of the present invention. In some embodiments of the present invention an oligomer may comprise at least one oligomer cassette and at least one flanking region of unrandomized positions. In other embodiments of the present invention an oligomer may be comprised of more than one cassette wherein each cassette is flanked by at least one region of randomized positions. For example, an oligonucleotide cassette of known sequence may be flanked at the 3' terminus, the 5' terminus, or both the 3' and 5' termini.

In some embodiments of the present invention it may also be desirable to subfractionate a group of oligomers to provide subfractions of the sets of oligomers, thus limiting the degree of complexity that is assayed at one time. This both diminishes the amount of total material that must be used in a determination in order to have sufficient representation of all individual sequences and it also enhances the signal to noise ratio of the assay by starting with oligomer sets enriched in the most active sequences. Any physicochemical or functional characteristic, combined with an appropriate separation modality may be used to empirically subfractionate a group, thereby resulting in (or deriving) numerous distinct subfractions of diverse character, and diminished complexity. It is theorized that if a particular sequence or sequences exist within the original group, that bind to a particular target, it will be found enriched in a limited number of the reduced complexity subfractions.

One skilled in the art would be apprised of the broad selection of appropriate selection modalities which are available. The strategy followed will, of course, depend upon the properties of the elements of the oligomer group. It will further be appreciated by one skilled in the art that as the number of group elements increases and the structural and chemical diversity enlarges, there will be a greater selection of separation strategies leading to increased subfractionation capacity. By way of example, it is envisioned that novel oligomers may be resolved into subfractions by any one or a combination of size, positive or negative charge, hydrophobicity and affinity interactions. Many chromatographic and analytical instrumental methods are known to those skilled in the art which may be effectively applied to the separation strategies encompassed herein.

In some embodiments of the invention, each set of oligomers is assayed for desired activity. In other embodiments of the present invention, identical empirical assays of subfractions of oligomer sets described above are performed in order to identify those subfractions having the strongest activity as indicated by a strong signal to noise ratio. The set having the highest activity or the set from which the subfraction having the highest activity is derived is selected and further unrandomization may be performed if desired.

Specific target activity may be detected by methods known to those skilled in the art. Appropriate assays will be apparent to one skilled in the art and oligomer concentration, target molecule concentration, salt concentration, temperature, buffer and buffer concentration may be altered to optimize a particular system. In some preferred embodiments of the present invention, binding conditions simulate physiological conditions. In other preferred embodiments of the present invention, binding occurs in a buffer of from about 80 mM to about 110 mM sodium chloride and from about 10 mM to about 15 mM magnesium chloride. Oligomers may also generally be assayed for enzyme inhibitory or catalytic activity. Illustrative cell-based assays and their brief descriptions are as follows:

HIV: CEM-SS cells are infected with live virus (HIV-1) in the presence of library subsets. The assay measures protection of the cells from virus-induced cytopathic effects for each set of oligomers.

Tumor Necrosis Factor (TNF): Each set of oligomers is assayed for its inhibition of TNF induction of inflammatory cascade in NHDF cells. ICAM-1 induction is determined to be the endpoint.

Interleukin 1-β (IL1-β): Each set of oligomers is assayed for its inhibition of IL1-β induction of inflammatory cascade in NHDF cells using ICAM-1 induction as endpoint.

Malaria: Each set of oligomers is assayed for its inhibition of parasite replication in blood cells.

Interleukin-6 (IL-6): Each set of oligomers is assayed for its inhibition of the interaction of IL-6 and its receptor expressed in live cells using an antibody specific for IL-6.

LTB$_4$: Each set of oligomers is assayed for its inhibition of the radiolabeled ligand interaction with membrane-bound receptor. The membrane is partially purified from guinea pig ileum.

PLA$_2$: Each set of oligomers is assayed for its inhibition of enzymatic activity of type II phospholipase A$_2$. The substrate is *E. coli* with a radiolabeled fatty acid in the membrane.

TAT/tar: Biotinylated tar RNA is bound to streptavidin-coated wells of a 96-well microtiter plate. Each set of oligomers is assayed for its inhibition of the interaction between tat protein and tar RNA by the library subsets using ELISA-type assay with a tat-specific antibody.

Gel shift assays may be used to visualize binding of an oligomer to a known target molecule. In accordance with methods of the present invention, radiolabeled target molecule bound to an oligomer of the present invention may be run on a gel such as a polyacrylamide gel. Bound target molecule has less mobility than unbound target molecule, and therefore will not migrate as far on the gel. The radioactive label allows visualization of the "shift" in mobility by standard procedures for example, by means of X-ray radiography or by using a phosphorimager (Molecular Dynamics, Sunnyvale, Calif.). In other embodiments of the present invention, a gel shift assay may be performed wherein an unlabeled target molecule may be bound to radiolabeled oligomer.

Radiolabeled oligomer may also be useful for the streptavidin capture of a biotinylated target bound to an oligomer. For example, a target may be biotinylated prior to incubation with radiolabeled random oligomer sets. Each set is thereafter incubated with the target under identical conditions and the target molecule is captured on streptavidin-coated beads. Consequently any oligomer which bound to the target will also be captured. Streptavidin-coated beads are available commercially such as for example, streptavidin-coated manganese particles available from Promega. The beads are washed and the reaction may be reequilibrated to further enrich the "winning" sequence. The percent of oligomers from each set which bound is determined by the amount of radioactivity remaining after washing. Measuring radioactivity in a sample may be performed by a number of methods known in the art. For example, the amount of radioactivity may be determined directly by counting each sample using, for example, a scintillation counter. Samples may also be run on a polyacrylamide gel, the gel may be placed under x-ray film and a densitometric reading of the autoradiogram may be taken. Alternatively, a phosphorimager (Moelcular Dynamics, Sunnyvale, Calif.) may be used to detect the radioactive signal in the gel.

In further embodiments of the present invention further groups of sets are prepared. Each of said further groups has a selected number of sets of oligomers. Each set of a further group has in a previously defined common position the monomer unit appearing in that position in the previously selected set. Each set of the further group has a different known monomer unit in an additional defined common position. The monomer units in the positions of the oligomer that are not in one of the defined common positions are randomized.

For example, in one group, the previously selected set may be comprised of an adenine in the previously defined common position. A further group is prepared with said adenine in said previously defined common position, and at another defined common position each set in said further group may be comprised of a different unit, either adenine, guanine, thymine or cytosine. The units in the positions of the oligomer that are not in a common position are randomized.

In further embodiments of the present invention, common positions are comprised of multiple oligomer positions as described above. For example, for a 9-mer, the one common position may be the third position of the 9-mer, or the common position may be comprised of the third position and the fourth position of the 9-mer.

SURF methodology may also be used with cyclic oligomers. For example, a macrocyclic amine may contain four substitution sites, i.e. site 1, site 2, site 3 and site 4, where one of seven monomer units A, B, C, D, E, F or G might be introduced. Site 1 may be chosen as the fixed position. Seven sets of cyclic oligomers are synthesized, each with a different monomer at site 1. The other sites comprise an equimolar mixture of all the monomers, A through G. The sets of cyclic oligomers are screened for desired specific activity, and the oligomer with optimal activity is identified. The sets of cyclic oligomers in the next round of synthesis contain the fixed monomer from the previous round and a second site is designated as the fixed position, e.g. site 2. Through successive rounds of screening and synthesis, a unique oligomer with desired specific activity may be identified. Circular oligonucleotides, for example Blumenfeld et al., WO 92/19732, can be similarly determined.

Procedures useful for increasing the complexity of an oligomer group, and/or increasing specific activity of an oligomer described previously are equally applicable to said further groups. Thus, oligomer groups may be comprised of multiple units, may be sterically constrained and may be subfractionated prior to assaying for specific activity. Furthermore, oligomers of further groups may comprise one or more cassettes.

Sets are again assayed for desired activity. The steps described above may be performed iteratively.

In other embodiments of the present invention, the specific activity of an oligomer determined according to the present invention may be further enhanced by "mutational" SURF.™ This involves "mutation" or replacement of at least one monomer unit at a defined position in the oligomer with a different monomer unit. The length of the oligomer may also be modified by the addition or deletion of at least one monomer unit. The oligomers are then screened for desired desired target activity, and the most active oligomer determined. This process may be repeated, preferably until no enhancement in specific activity is observed.

In still other embodiments of this invention, the determination of an oligomer with desired specific activity may also be achieved by the generation of a library of compounds of decreased complexity. This method involves the identification of optimal monomers prior to the process of synthetic unrandomization. According to this embodiment, "subtractive" sets of completely random oligomers are prepared. A group of monomer units is selected and sets of randomized oligomers are synthesized. Each set is synthesized using all but at least one defined monomer unit from said group of selected monomer units, the excluded monomer or monomers being different in each set of randomer oligomers. The sets of oligomers are assayed for target activity and the sets of oligomers have little or no target activity are selected, whereby the monomer unit excluded from the selected set or sets is identified as being critical for the target activity of interest. This method allows screening of simplified libraries and rapid determination of an active oligomer from a library of oligomers, and is particularly useful where the number of monomers to be used for the synthesis of libraries is greater than the oligomer length (i.e. the number of monomers in the oligomer).

Compounds of the present invention include monomer units of structure I:

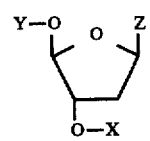

Structure I wherein:

X is H, a phosphate group, an activated phosphate group, an activated phosphite group, or a solid support;

Y is H, or a hydroxyl protecting group; and Z is structure II:

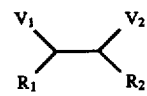

Structure II wherein:

$R_1$ and $R_2$, together, form a five-membered heterocycle containing 1 to 3 nitrogen atoms, the remaining atoms being carbon atoms, and is connected to the pentofuranosyl ring of the compound of structure I via one of the said nitrogen atoms;

$V_1$ and $V_2$ are linked together forming a six-membered ring and are CH=CH—CH=CH, C(NH)—NH—NH—C(NH), C(O)—NH—NH—C(O), CH (NH$_2$)—NH—NH—C(O), C(O)—NH—NH—CH(NH$_2$), or CH (NH$_2$)—NH—NH—CH(NH$_2$); or $V_1$ and $V_2$ are, independently, C(O)—NH$_2$, or C(O)OV$_3$, where $V_3$ is alkyl having 1 to about 5 carbon atoms.

In preferred embodiments, Y is an acid labile hydroxyl blocking group such as trityl, methoxytrityl, dimethoxytrityl or trimethoxytrityl group. X preferably is a phosphoramidite. $R_1$ and $R_2$ preferably form a pyrrole or a triazole. Oligomers comprising one or more of such monomers are also provided in accordance some embodiments of the present invention.

The following examples are illustrative, but not limiting of the invention.

EXAMPLE 1

Synthesis of DNA Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl phosphoramidites may be purchased from Applied Biosystems (Foster City, Calif.).

EXAMPLE 2

Synthesis of RNA Oligonucleotides

Unmodified RNA oligonucleotides having random base sequences were synthesized on an automated DNA synthesizer (Applied Biosystems model 380B) using modified standard phosphoramidite chemistry synthesis with oxidation by iodine. The standard synthesis was modified by increasing the wait step after the pulse delivery of tetrazole to 900 seconds. β-cyanoethyldiisopropyl phosphoramidites were purchased from Applied Biosystems (Foster City, Calif.). The bases were deprotected by incubation in methanolic ammonia overnight. Following base deprotection, the oligonucleotides were dried in vacuo. The t-butyldimethylsilyl protecting the 2' hydroxyl was removed by incubating the oligonucleotide in 1M tetrabutylammoniumfluoride in tetrahydrofuran overnight. The RNA oligonucleotides were further purified on $C_{18}$ Sep-Pak cartridges

17

(Waters, Division of Millipore Corp., Milford, Mass.) and ethanol precipitated.

EXAMPLE 3

Synthesis of Phosphorothioate Oligonucleotides

Phosphorothioate oligonucleotides represent a class of oligorecleotide analogs that is substantially nuclease resistant. Phosphorothioate RNA oligonucleotides and phosphorothioate DNA oligonucleotides were synthesized according to the procedure set forth in Examples 1 and 2 respectively, replacing the standard oxidation bottle by a 0.2M solution of 3H-1,2-benzodithiole-3-one-1,1-dioxide in acetonitrile for stepwise thiation of phosphite linkages. The thiation cycle wait step was increased to 68 seconds and is followed by the capping step.

EXAMPLE 4

Synthesis of 2'-O-alkyl Phosphorothioate Oligonucleotides

2'-O-methyl phosphorothioate oligonucleotides were synthesized according to the procedures set forth in Example 3 substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl, 2'-O-phenyl and 2'-O-nonyl phosphorothioate oligonucleotides were prepared by slight modifications of this procedure.

EXAMPLE 5

Preparation of Pyrene Oligonucleotide Analogs

Oligonucleotides were prepared by incorporating 2' aminopentoxyadenosine at desired sites. The oligonucleotides were dissolved in 0.2M NaHCO$_3$ buffer and treated with 50 fold excess of N-hydroxysuccinimide ester of pyrene-1-butyric acid dissolved in dimethylformamide. The resultant mixture was incubated at 37° C. for 4–5 hours and the conjugate was purified by reverse phase HPLC followed by desalting in a G-25 Sephadex column.

EXAMPLE 6

Synthesis of Oligonucleotide Having Randomized Positions

Four columns of the DNA synthesizer were packed with a mixture containing an equal amount of adenosine(A)-, cytidine(C)-, guanosine(G)- and uracil(U)-controlled pore glass (CPG, Chemgenes, Needham, Mass.). At coupling steps where a given nucleotide base was desired, the defined phosphoramidite was delivered to each column. At each "random" coupling step, an equimolar mixture of all four phosphoramidites was delivered to each column.

EXAMPLE 7

Preparation of Radiolabeled Groups

Oligonucleotide groups prepared in accordance with [γ-$^{32}$P] ATP and T4 Example 1 through 6 are radiolabeled using polynucleotide kinase as described in Sambrook et al. "Molecular Cloning: A Laboratory Manual," Cold Spring Harbor Laboratory Press, 1989, Volume 2, pg. 11.31–11.32.

EXAMPLE 8

Effect of Site of Unrandomization on Activity

Twenty-four sets of phosphorothioate oligonucleotides were prepared in accordance with Examples 3 and 6 as set forth in Table 2.

TABLE 2

| Set 1  | ANNNNN | Set 13 | NNNANN |
| Set 2  | CNNNNN | Set 14 | NNNCNN |
| Set 3  | GNNNNN | Set 15 | NNNGNN |
| Set 4  | TNNNNN | Set 16 | NNNTNN |
| Set 5  | NANNNN | Set 17 | NNNNAN |
| Set 6  | NCNNNN | Set 18 | NNNNCN |
| Set 7  | NGNNNN | Set 19 | NNNNGN |
| Set 8  | NTNNNN | Set 20 | NNNNTN |
| Set 9  | NNANNN | Set 21 | NNNNNA |
| Set 10 | NNCNNN | Set 22 | NNNNNC |
| Set 11 | NNGNNN | Set 23 | NNNNNG |
| Set 12 | NNTNNN | Set 24 | NNNNNT |

Each of the sets is tested for activity against a target molecule to determine which order of unrandomization gives the highest initial specific activity.

EXAMPLE 9

Preparation of a Biotin Oligonucleotide Group

An oligonucleotide group having the sequence TNNNXNNNTB, wherein N is a mixture of A, G, C, or U, X is one of A, G, C and U and B is biotin, is prepared in accordance with Examples 3 and 6. The sequence is designed with flanking thymidines to provide sites for radiolabeling. A control having the sequence TNNNX-NNNT is also prepared in accordance with Examples 3 and 6.

EXAMPLE 10

Preparation of Oligonucleotide Group comprising Nucleotide Analogs.

Oligonucleotide groups having the sequence NNNX-NNNU are prepared in accordance with Example 1 and 6 incorporating one or more of the nucleoside analogs 2'-O-nonyl adenosine, N6-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine and 6-amino-2-hydroxylmethyl-1-hexanol. The nucleosides, 2'-O-nonyl adenosine, N6-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine were prepared by modification of the methods described in PCT US91/00243 filed Jan. 11, 1991. 6-amino-2-hydroxylmethyl-1-hexanol is available commercially. The nucleosides are modified to provide the corresponding phosphoramidite by methods known to those skilled in the art.

EXAMPLE 11

Synthesis of 1-(1-Thymine)-3-O-dimethoxytrityl-2-O-[(N, N-diisopropylamino)-2-cyanoethoxyphosphite]propane (egpT)

To a stirred solution of thymine (4.2 g, 33 mmol) in anhydrous dimethylformamide (30 mL), was added glycidol (2.2 g, 30 mmol) and potassium carbonate (50 mg, 0.36 mmol). The suspension was heated at 80° C. for 5 hours, then evaporated. The product was diluted with methanol (25 mL) and filtered. The filtrate was evaporated and the residue purified by silica gel column chromatography. Elution with ethyl acetate:methanol (9:1), pooling of appropriate fractions and evaporation of solvent furnished 3.08 g (60%) of 1-(1-thymine)-2,3-propanediol (free from the $N_1,N_3$-disubstituted material).

To a stirred solution of 1-(1-thymine)-2,3-propanediol (2.079 g, 12.4 mmol) in anhydrous pyridine (30 mL) was added 4,4'-dimethoxytrityl chloride (4.4 g, 13 mmol). The suspension was stirred at room temperature for 4 hours. The reaction mixture was evaporated and the residue purified by silica gel column chromatography. Elution with ethyl acetate:hexane:triethylamine (3:2:1), pooling of appropriate fractions and evaporation of solvent gave 3.39 g (54%) of 1-(1-thymine)-3-O-dimethoxytrityl-2-propanol.

A stirred solution of 1-(1-thymine)-3-O-dimethoxytrityl-2-propanol (3.39 g, 6.7 mmol) and N,N-diisopropylethylamine (2.4 mL, 14 mmol) in anhydrous tetrahydrofuran (35 mL) was cooled to 10° C. in an ice bath. Chloro-β-cyanoethoxy-N,N-diisopropylaminophosphine (1.5 mL, 6.7 mmol) was added. After stirring at room temperature for 4 hours, the reaction mixture was evaporated and the residue purified by silica gel column chromatography. Elution with ethyl acetate:hexane:triethylamine (1:1:1), pooling of appropriate fractions and evaporation of solvent provided a yield of 2.78 g (61%) of the title compound.

EXAMPLE 12

Synthesis of 1-(1-Imidazole)-3-O-dimethoxytrityl-2-O-[(N,N-diisopropylamino)-2-cyanoethoxyphosphite]propane (egpIM)

A rapidly stirred solution of imidazole (13.6 g, 0.2 mol) in dimethylformamide (250 mL0 was treated with powdered potassium carbonate (12 g) and heated at 70° C. for 30 minutes. To this solution was added glycidol (14.8 g, 0.2 mol) in one portion, and the mixture stirred for 36 hours. The resulting yellow suspension was filtered, and the filtrate evaporated to afford a clear red syrup. This material was coevaporated with acetonitrile (100 mL) and then purified by flash column chromatography on a 10.5×10 cm silica gel column. A step gradient elution of ethyl acetate:methanol (9:1, 2 L, then 4:1, 2 L) provided 16 g (56%) of the product, 1-(1-imidazole)-2,3-propanediol, as an amorphous solid.

To a stirred solution of 1-(1-imidazole)-2,3-propanediol (1.0 g, 7.0 mmol) in anhydrous pyridine (15 mL) and anhydrous dimethylformamide (15 mL) was added 4,4'-dimethoxytrityl chloride (2.61 g, 7.7 mmol). The suspension was stirred at room temperature for 4 hours. An additional equivalent of the trityl compound (2.61 g, 7.7 mmol) was added. Stirring was continued for an additional 23 hours and the mixture evaporated. The residue was purified by silica gel column chromatography. Elution with methanol:ethyl acetate:triethylamine (1:19:1), pooling of appropriate fractions and evaporation of solvent yielded 432 mg (14%) of 1-(1-imidazole)-3-O-dimethoxytrityl-2-propanol.

A solution of 1-(1-imidazole)-3-O-dimethoxytrityl-2-propanol (432 mg, 0.97 mmol) and N,N-diisopropylethylamine (252 mg, 3.5 mmol) in anhydrous dimethylformamide (35 mL) was cooled to 5° C. in an ice bath. Chloro-5-cyanoethoxy-N,N-diisopropylaminophosphine (233 mg, 1.1 mmol) was added and the reaction mixture stirred at room temperature for 1 hour. The reaction mixture was then evaporated and the residue purified by silica gel column chromatography. Elution with ethyl acetate:hexane:triethylamine (7:3:1), pooling of appropriate fractions and evaporation of solvent provided a yield of 498 mg (80%) of the desired product.

EXAMPLE 13

Synthesis of 1-(1-Carbazole)-3-O-dimethoxytrityl-2-O-[(N,N-diisopropylamino)-2-cyanoethoxyphosphite]propane (egpCB)

A rapidly stirred solution of carbazole (14 g, 83 mmol) and glycidol (6.20 g, 83 mmol) in anhydrous dimethylformamide (300 mL) was treated with powdered potassium carbonate (2.3 g). The mixture was heated to 70° C. for 18 hours. The resulting yellow suspension was filtered and the solvent evaporated to afford a yellow syrup. The syrup was coevaporated with acetonitrile (100 mL) and purified by flash chromatography on a 10.5×10 cm silica gel column. Elution with ethyl acetate gave 1-(1-carbazole)-2,3-propanediol as an amorphous solid (8.25 g, 41%).

The diol product (1.1 g, 4.5 mmol) was dissolved in pyridine (40 mL) and 1,54 g (4.5 retool) of 4,4'-dimethoxytritylchloride added. The reaction mixture was stirred at room temperature for 3 hours and the solvent evaporated. The residue was purified by silica gel column chromatography. Elution with ethyl acetate provided 976 mg (39%) of 1-(1-carbazole)-3-O-dimethoxytrityl-2-propanol.

Chloro-β-cyanoethoxy-N,N-diisopropylaminophosphine (403 mg, 1.7 mmol) was added to a solution of 1-(1-carbazole)-3-O-dimethoxytrityl-2-propanol (916 mg, 1.7 mmol) and N,N-diisopropylethylamine (445 mg, 3.4 mmol) in dry tetrahydrofuran (40 mL) at 5° C. for 4 hours. The solvent was evaporated and the residue purified by silica gel column chromatography. Elution with ethyl acetate:hexane:triethylamine (1:19:1), pooling of appropriate fractions and evaporation of solvent afforded 850 mg (68%) of 1-(1-carbazole)-3-O-dimethoxytrityl-2-O-[(N,N-diisopropylamino)-2-cyanoethoxyphosphite]propane.

EXAMPLE 14

Synthesis of random ethylene glycol phosphate oligomeric libraries

EGP phosphoramidites of monomer units such as adenine (egpA), guanine (egpG), cytosine (egpC), thymine (egpT), carbazole (egpCB) and imidazole (egpIM) were synthesized according to the procedures described in Examples 11, 12 and 13. Equimolar amounts of selected EGP phosphoramidites were dissolved in anhydrous acetonitrile to 0.2M, with the exception of EGP-guanine (egpG) which was first dissolved in anhydrous dimethylformamide to 2M and then further diluted to 0.2M with anhydrous acetonitrile. EGP phosphoramidites were coupled to a 1–2 μmol CPG support on an ABI 394 DNA synthesizer using the standard ABI cycle for a 1 μmol scale cyanoethylphosphoramidite synthesis with the coupling wait time increased to 5 minutes. By substituting a 0.1M solution of 3H-1,2-benzodithiol-3-one-1,1-dioxide (Beaucage reagent) in acetonitrile for the iodine oxidizing solution, phosphorothioate oligomers were also synthesized. The 5'-dimethoxytrityl group (DMT) of an oligomer terminating in a 5'-EGP residue was not removed prior to cleaving the oligomer from the CPG support. Detritylation of oligomer before cleavage with ammonium hydroxide from CPG results in the hydrolysis of the 5'-EGP residue as a cyclic phosphate.

EGP oligomers were cleaved from CPG in 1 mL of 30% ammonium hydroxide, for 1 hour at room temperature. Cleaved oligomer was deprotected using ammonium hydroxide at 55° C. for 12–18 hours. Ammonium hydroxide was then removed from the reaction mixture by evaporation in a Savant speedvac. The 5'-hydroxyl was deprotected by cleaving the DMT group from the oligomer in 1 mL of 80% acetic acid for 1 hour. Acetic acid was then removed from the reaction mixture by evaporation in a speedvac.

The oligomers were resuspended in water and further purified by one or more of the methods described in Example 15.

EXAMPLE 15

General oligomer purification procedures

Procedure A: reverse phase HPLC

To desalt by reverse phase HPLC, the oligomer was loaded onto a reverse phase HPLC column in approximately 100 mM ammonium acetate or sodium acetate. The column was washed with several column volumes (10–20) of water to desalt. The oligomer was eluted in a gradient of 0% to 100% methanol.

Procedure B: size exclusion chromatography

To desalt by size exclusion chromatography, the oligomer was loaded onto a size exclusion chromatography column, typically Sephadex G10 or G25, 1.6×50 cm, that is conected to an HPLC instrument and eluted in water at a flow rate of 0.5 mL/minute. The oligomer elutes from the column in approximately 2–3 hours, followed by salts and protecting groups.

Procedure C: ethyl acetate extraction

The oligomers may also be purified from the protecting groups by ethyl acetate extraction. However, this method does not desalt the oligomer. After DMT cleavage with acetic acid, the dried oligomer was resuspended in 1–2 mL of water. Ethyl acetate (1 mL) was added to the oligomer and vortexed to mix the layers. After separation of the water and ethyl acetate layers, the organic (ethyl acetate) layer, containing the protecting groups, was removed from the water layer containing the oligomer.

After purification by chromatography or extraction, the oligomer was dried by evaporation in the speedvac. The oligomer was resuspended in water (0.5–2 mM) and stored at −20° C.

EXAMPLE 16

Synthesis of 5-dimethoxytrityloxymethyl-3-hydroxypyrrolidine

Hydroxyproline (5.0 g, 38.2 mmol) and sodium bicarbonate (8.0 g, 95.2 mmol) were suspended in 150 mL of water:dioxane (1:1). Fluorenylmethyl chloroformate (11.4 g, 44.0 mmol) in 25 mL of toluene was added dropwise. The temperature of the reaction was not allowed to rise above 25° C. during the addition. The mixture was stirred vigorously overnight, and then quenched with saturated sodium bicarbonate (50 mL) and water (50 mL). The solution was then extracted with diethyl ether (100 mL). The aqueous layer was acidified to pH 1 with concentrated HCl and extracted twice with ethyl acetate. The organic extracts were washed with brine. The solution was then dried with anhydrous magnesium sulfate, filtered and the solvent removed in vacuo. After crystallization, 13.4 g (100%) of pure N-Fmoc-trans-4-hydroxy-L-proline was obtained.

To a solution of hydroxyproline (13.4 g, 38.1 mmol) in 250 mL tetrahydrofuran was added borane-methyl sulfide (5.78 g, 7.22 mL, 78 mmol) dropwise at room temperature. After the evolution of $H_2$ had ceased, the solution was heated to reflux. A white precipitate formed after 1 hour. Methanol was carefully added, and the resulting solution refluxed for an additional 15 minutes. The solution was cooled to room temperature, solvent evaporated under reduced pressure and the residual gum coevaporated with 2×100 mL of methanol. The resulting crystalline product, $N^1$-Fmoc-3-hydroxypyrrolidine-5-methanol, weighed 12 g (93%).

$N^1$-Fmoc-3-Hydroxypyrrolidine-5-methanol (12.0 g, 35.3 mmol) was coevaporated with anhydrous pyridine (2×50 mL), redissolved in 200 mL of anhydrous pyridine and cooled in an ice bath. Dimethoxytrityl chloride (13.6 g, 38 mmol) was added in portions over 15 minutes, and the solution stirred at room temperature for 12 hours. Methanol (10 mL) was then added and the solvent evaporated under reduced pressure. The resulting gum was dissolved in toluene (100 mL), filtered to remove pyridinium hydrochloride and evaporated to dryness. The residue was triturated with ether/hexane to produce a tan solid, and chromatographed (0 to 1.5% methanol/dichloromethane) to provide 14.85 g (66%) of $N^1$-Fmoc-5-dimethoxytrityloxymethyl-3-hydroxypyrrolidine. Alternatively, the product could be crystallized from hexane:ethyl acetate (2:1).

To a solution of the carbamate obtained above (3.40 g, 5.3 mmol in 15 mL of dimethylformamide) was added piperidine (0.935 g, 1.09 mL, 11.0 mmol). The solution was stirred at room temperature for 1 hour. Water (100 mL) was then added, and the aqueous solution extracted with ethyl acetate (2×75 mL). The organic extracts were washed with aqueous sodium bicarbonate and brine, and then dried with anhydrous magnesium sulfate and evaporated under reduced pressure. The residue was purified by flash column chromatography using a gradient of 1% to 3% methanol in dichloromethane containing 0.5% of triethylamine. Pure product was obtained (1.86 g, 84%).

EXAMPLE 17

Synthesis of $N^1$-Palmitoyl-5-dimethoxytrityloxymethyl-3-hydroxypyrrolidine

To the amino alcohol of Example 16 (0.50 g, 1.19 mmol) dissolved in 5 mL of anhydrous pyridine was added chlorotrimethylsilane (194 mg, 0.227 mL, 1.79 mmol), with stirring for 1 hour. The carboxylic component (e.g. palmitic acid, 209 mg, 1.55 mmol), hydroxybenzotriazole (209 mg, 1.55 mmol) and dimethylaminopropylethyl carbodiimide (EDC, 281 mg, 1.80 mmol) were dissolved in dimethylformamide (5 mL) and stirred for 1 hour. This solution was then added to the pyridine solution of the amino alcohol and stirred until the complete disappearance of starting material. The reaction was halted by the addition of 5 mL of saturated sodium bicarbonate, and after 15 minutes the solution was diluted with water (100 mL), extracted with ethyl acetate (2×75 mL), washed with sodium bicarbonate, brine, dried and evaporated. The product was purified by silica gel column chromatography using ethyl acetate/hexane as the eluant. The product was identified by $^1$H NMR in $CDCl_3$.

EXAMPLE 18

Synthesis of $N^1$-Isobutyroyl-5-dimethoxytrityloxymethyl-3-hydroxypyrrolidine

This compound was prepared as per the procedure described in Example 17 by the use of isobutyric acid as the carboxylic component. The product was identified by $^1$H NMR in $CDCl_3$.

EXAMPLE 19

Synthesis of $N^1$-[(N1-Thymidine)-2-acetyl]-5-dimethoxytrityloxymethyl-3-hydroxypyrrolidine This compound was prepared as per the procedure described in Example 17 by the use of thymidine-2-acetic acid as the carboxylic acid component. The product was identified by $^1$H NMR in DMSO-$d_6$.

EXAMPLE 20

Synthesis of $N^1$-[(N4-Benzoyl-1-cytosine)-2-acetyl]-5-dimethoxyytrityloxy-methyl-3-hydroxypyrrolidine The title compound is prepared via the procedure described in Example 17 using N4-benzoyl-1-cytosine-2- acetic acid as the carboxylic acid component. The product is identified by $^1$H NMR.

EXAMPLE 21

Synthesis of $N^1$-Palmitoyl-5-dimethoxytrityloxymethylpyrrolidine-3-O-[(N,N-diisopropylamino)-2-cyanoethoxy-phosphite] (hppPa)

To a solution of $N^1$-palmitoyl-5-dimethoxytrityloxymethyl-3-hydroxypyrrolidine in dichloromethane (0.1M) at 0° C. was added 3 equivalents of diisopropylethylamine, followed by 1.1 equivalents of 2-cyanoethyl-N,N-diisopropylaminochlorophosphite. The solution was stirred at 0° C. until all the starting material was consumed. The solvent was removed in vacuo at low temperature and the resulting oil purified by flash column chromatography using ethyl acetate/dichloromethane containing 1% triethylamine as eluant.

EXAMPLE 22

Synthesis of $N^1$-[(N1-Thymidine)-2-acetyl]-5-dimethoxytrityloxymethyl-3 $N^1$-dimethoxytrityloxymethylpyrrolidine-3-O-[(N,N-diisopropyl-amino)-2-cyanoethoxyphosphite] (hppT)

The title compound was prepared as per the procedure of Example 21 using $N^1$-[(N1-thymidine)-2-acetyl]-5-dimethoxytrityloxymethyl-3-hydroxypyrrolidine of Example 41 as the starting material.

EXAMPLE 23

Synthesis of $N^1$-(Isobutyroyl)-dimethoxytrityloxymethylpyrrolidine-3-O-[(N,N-diisopropylamino)-2-cyanoethoxyphosphite]

The title compound was prepared as per the procedure of Example 21 using $N^1$-(isobutyroyl)-5-dimethoxytrityloxymethyl-3-hydroxypyrrolidine of Example 40 as the starting material.

EXAMPLE 24

Synthesis of random hydroxypyrrolidine phosphate oligomeric library

HPP phosphoramidites were synthesized according to the procedures described in Examples 21, 22, and 23. Examples of some HPP phosphoramidites are adenine (hppA), guanine (hppG), cytosine (hppC), thymine (hppT), palmitic acid (hppPa) and isobutyric acid (hppIB). The HPP oligomeric molecules were synthesized on an automated DNA synthesizer (Applied Biosystems model 380B). For phosphorothioate oligomers, the standard iodine oxidation solution was replaced by 0.2M solution of 3H-1,2-benzodithiol-3-one-1, 1-dioxide in acetonitrile for the stepwise thiation of the phosphite linkages. The thiation wait step was increased to 68 seconds and was followed by the capping step. After cleavage from the CPG column and deblocking with concentrated ammonium hydroxide at 55° C. for 18 hours, the oligomers were purified by precipitation (twice) from 0.5M NaCl solution with 2.5 volumes of ethanol. Analytical gel electrophoresis was effected in 20% acrylamide, 8M urea and 454 mM Tris-borate buffer at pH 7.0.

EXAMPLE 25

Synthesis of 2-(2'-deoxy-β-D-erythro-pentofuranosyl)-2H-benzotriazole and1-(2'-deoxy-β-D-erythro-pentofuranosyl)-1H-benzotriazole To a stirred suspension of sodium hydride (60% in oil, 2 g, 50 mmol) in anhydrous acetonitrile (200 mL) was added benzotriazole (5.95 g, 50 mmol) in one portion, with care, under argon at room temperature. The suspension was stirred at room temperature for 30 minutes. Finely powdered 2-deoxy-3,5-di-O-p-toluoyl-α-D-erythro-pentofuranosyl chloride (19.4 g, 50 mmol) was added in portions over 15 minutes. The reaction mixture was stirred at room temperature for 3 hours and then filtered. The crystalline material was washed with acetonitrile (2×50 mL) and water (2×50 mL), and dried under reduced pressure to yield 6.81 g of 2-(2'-deoxy-3',5'-di-O-p-toluoyl-β-D-erythro-pentofuranosyl)-2H-benzotriazole as a white powder. The combined filtrates were concentrated under reduced pressure to furnish a gummy residue (7.12 g). The residue was extracted into dichloromethane (300 mL), washed with water and dried with anhydrous magnesium sulfate. The organic layer was concentrated and the residue purified by silica gel column chromatography. Elution with hexanes:ethyl acetate (7:3) furnished, evaporation of solvent and crystallization from ethanol provided 4.68 g (20%) of 1-(2'-deoxy-3',5'-di-O-p-toluoyl-β-D-erythro-pentofuranosyl)-2H-benzotriazole. Further elution with polar solvent, pooling of appropriate fractions and evaporation of solvent gave 2.4 g (total yield of 36%) of 2-(2'-deoxy-3',5'-di-O-p-toluoyl-β-D-erythro-pentofuranosyl)-2H-benzotriazole.

The 3'- and 5'-hydroxyl groups were deblocked, i.e. the 3'- and 5'-toluoyl groups were removed, by the addition of a methanolic solution of sodium methoxide (25%, 2 mL) to a solution of 2-(2'-deoxy-3',5'-di-O-p-toluoyl-β-D-erythro-pentofuranosyl)-2H-benzotriazole (5.12 g, 10.87 mmol) until the pH of the solution was 9. The alkaline solution was stirred at room temperature for 2 hours, neutralized with Dowex-50 (H$^+$) resin and filtered. The filtrate was evaporated to dryness, and the residue triturated with hexanes (3×50 mL) and crystallized from dichloromethane to provide 2.9.6 g (88.6%) of the N-2 isomer, 2-(2'-deoxy-β-D-erythro-pentofuranosyl)-2H-benzotriazole. $^1$H NMR: (DMSO-d$_6$) δ 2.45 (m, 1, 2'H), 3.01 (m, 1, 2'H), 4.8 (broad s, 1, 5'OH), 5.4 (broad s, 1, 3'OH), 7.40–8.11 (m, 4, benzotriazole H). Anal. calc. for $C_{11}H_{13}N_3$: C, 56.16; H, 5.56; N, 17.86; Found: C, 56.09; H, 5.42; N, 18.11. The N-1 blocked isomer, 1-(2'-deoxy-3',5'-di-O-p-toluoyl-β-D-erythro-pentofuranosyl)-2H-benzotriazole, was deblocked in a similar manner furnishing 1.91 g (75%) of 1-(2'-deoxy-β-D-erythro-pentofuranosyl)-2H-benzotriazole. $^1$H NMR: (DMSO-d$_6$) δ 2.44 (m, 1, 2'H), 2.93 (m, 1, 2'H), 4.75 (t, 1, 5'OH), 5.41 (d, 1, 3'OH), 7.43 and 7.95 (2d, 4, benzotriazole H).

EXAMPLE 26

Synthesis of diethyl 1-(2'-deoxy-β-D-erythro-pentofuranosyl)pyrrole-3,4-dicarboxylate To a stirred suspension of sodium hydride (60% in oil, 0.80 g, 20 mmol) in dry acetonitrile (100 mL) was added diethyl pyrrole-3,4-dicarboxylate (4.22 g, 20 mmol) and the reaction mixture stirred for 5 minutes. To this mixture was added finely powdered 2-deoxy-3,5-di-O-p-toluoyl-α-D-erythro-pentofuranosyl chloride (7.76 g, 20 mmol) in one portion and stirred for 3 hours at room temperature. The solid material formed was filtered, and the filtrate evaporated under reduced pressure. The residue was purified by silica gel column chromatography where elution with hexanes:ethyl acetate (1:1) gave 6.61 g of diethyl 1-(2'-deoxy-3',5'-di-O-p-toluoyl-β-D-erythro-pentofuranosyl)pyrrole-3,4-dicarboxylate (59%). Anal. calc. for $C_{31}H_{33}NO_9$: C, 66.06; H, 5.90; N, 2.48; Found: C, 65.57; H, 5.73; N, 2.28. This product (2.3 g, 4.1 mmol) was dissolved in anhydrous methanol (50 mL) and treated with a methanolic solution of sodium methoxide (25%, 0.5 mL). The solution was stirred at room temperature for 12 hours, neutralized with Dowex-50 (H⁺) resin and filtered. The resin was washed with methanol (2×20 mL) and the filtrate concentrated to a gummy residue, which was washed with warm hexanes and purified by silica gel column chromatography. Elution with dichloromethane:methanol (9:1), pooling of appropriate fractions and evaporation of solvent under reduced pressure furnished 1.3 g (97%) of the title compound.

EXAMPLE 27

Synthesis of dimethyl 2-(2'-deoxy-β-D-erythro-pentofuranosyl)-triazole-4,5-dicarboxylate A mixture of dimethyl 1,2,3-triazole-4,5-dicarboxylate (5 g, 27 mmol) and chlorotrimethylsilane (0.1 mL) in hexamethyldisilazane (HMDS, 15 mL) was heated under reflux for 3 hours. Excess HMDS was removed under reduced pressure and the residue was dissolved in anhydrous dichloromethane (300 mL). Dry, powdered 2-deoxy-3,5-di-O-p-toluoyl-α-D-erythro-pentofuranosyl chloride (10.48 g, 27 mmol) was added to the stirred reaction mixture in portions over 15 minutes. Powdered CuI (5.13 g, 27 mmol) was added to the reaction mixture in one portion at room temperature, and the suspension stirred at room temperature for 4 hours. The mixture was filtered through celite into a flask containing saturated sodium bicarbonate solution (100 mL). The residue was washed with dichloromethane (2×30 mL), water and dried with anhydrous magnesium sulfate. The organic layer was evaporated under reduced pressure and the residue purified by silica gel column chromatography to provide 8.18 g (56%) of dimethyl 2-(2'-deoxy-3',5'-di-O-p-toluoyl-β-D-erythro-pentofuranosyl)triazole-4,5-dicarboxylate. This product was dissolved in anhydrous methanol and a methanolic solution of sodium methoxide was added to the mixture. The alkaline solution was stirred for 2 hours at room temperature followed by neutralization with Dowex-50 (H⁺) resin and filtration. The filtrate was evaporated to dryness under reduced pressure, triturated with hexanes and purified by silica gel column chromatography to afford the title compound. ¹H NMR: (DMSO-d₆) δ 2.55–2.65 (m, 1, 2'H), 2.75–2.8 (m, 1, 2'H), 3.88 (s, 6, COOCH₃), 4.75 (t, 1, 5'OH), 5.2 (d, 1, 3'OH).

EXAMPLE 28

Gel-shift Assay of Random 2-O-Methyl Oligonucleotide Binding to ras RNA Target

The ras 47-mer stem/loop RNA was enzymatically synthesized, ³²P end-labeled according to standard procedures, and gel-purified. 2'-O-Methyl oligonucleotide analog libraries comprising four sets were prepared in accordance with Examples 4 and 6. Each set was tested for binding against the RNA target and a "set $K_D$" was determined in accordance with the following procedure.

In a first round the ras RNA target was incubated at a concentration of approximately 10 pM with each of the four random 2'-O-methyl oligonucleotide sets, at concentrations of 5, 10, 50 and 100 µM in a buffer consisting of 100 mM NaCl and 10 mM MgCl₂. The hybridization was carried out for four hours at 37° C., followed by electrophoretic separation of bound vs. unbound material on a 20% acrylamide gel in Tris-Borate buffer (TBE) plus 50 mM NaCl, run at 25 W for four hours. The gel was dried and the radioactive bands were visualized on a Phosphorimager (Molecular Dynamics, Sunnyvale, Calif.). The ras stem/loop target alone is the lowest band visible on the gel (highest mobility). As this target binds oligonucleotide (non-radioactive), the mobility of the ras target is decreased, shifting the band to a higher position on the gel (complex). In FIG. 2A no binding is seen for the oligonucleotide sets NNNNGNNNN or NNNNUNNNN, but NNNNANNNN shows a slight shift at 100 uM and NNNNCNNNN shifts more than 50% of the target to the bound form at 50 uM oligonucleotide concentration.

Figure 2B:
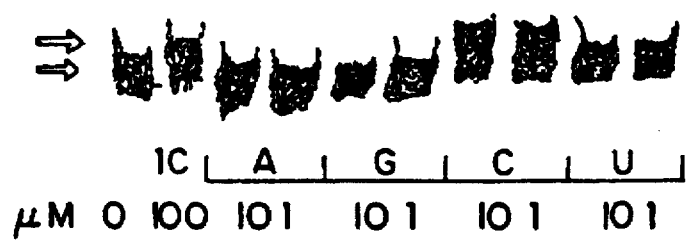
Figure 2C:
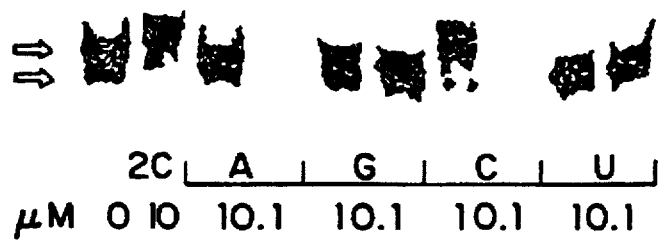

The protocol was then repeated in round 2. The ras RNA target was incubated at a concentration of approximately 10 pM with each of the four random oligonucleotide sets synthesized according to the method described above, at concentrations of 1 and 10 µM to provide the gel image of FIG. 2B which shows that oligonucleotide sets NNNNCNANN, NNNNCNGNN and NNNNCNUNN show minimal binding. NNNNCNCNN shows a shift of more than 25% of the target at 1 µM and about 50% of the target at 10 µM. In round 3 the ras RNA target was incubated with the random oligonucleotide sets at concentrations of 0.1 and 1 µM to provide the gel image of FIG. 2C where only NNCNCNCNN showed binding, exhibited by a shift of greater than 50% of the target.

Table 3 sets forth results of nine rounds performed to determine the "winner" sequence which binds to the ras RNA target. $K_D$ are in µM.

TABLE 3

| | | | Kd when X = | | | |
|---|---|---|---|---|---|---|
| Round | Sequence* | Q** | A | C | G | U |
| 1 | NNNNXNNNN | 65,536 | 22 | 10 | >100 | >100 |
| 2 | NNNNCNXNN | 16,384 | >10 | 4 | >10 | >10 |
| 3 | NNXNCNCNN | 4,096 | >10 | 0.5 | >10 | >10 |
| 4 | NNCXCNCNN | 1,024 | >10 | 0.15 | >10 | >10 |
| 5 | NNCCCXCNN | 256 | 0.08 | >1 | 0.4 | >1 |
| 6 | NNCCCACXN | 64 | 0.05 | >0.5 | 0.08 | >0.5 |
| 7 | NXCCCACAN | 16 | >0.1 | >0.1 | 0.03 | >0.1 |
| 8 | NGCCCACAX | 4 | 0.05 | 0.02 | 0.05 | 0.042 |
| 9 | XGCCCACAC | 1 | 0.03 | 0.05 | 0.02 | 0.01 |

*wherein N is a mixture of A, C, G and T;
**Q is set complexity.

As illustrated in Table 3, it was not difficult to distinguish the set with the lowest $K_D$ (µM) at each round of synthesis and screening.

As expected for oligonucleotide hybridization reactions, positions near the center of the oligonucleotide had a greater effect on the $K_D$ than positions on the extreme 5' or 3' ends. For example, an attempt to fix the 3' position in round 4 did not yield results that distinguished the sets. An alternative position was selected for round 4 which yielded a clear winner, and then the sequence was elucidated from the center of the oligomer to the ends. The final oligonucleotide selected by the procedure is complementary to the single stranded loop region of the target RNA.

EXAMPLE 29

ELISA for Detection of Inhibition of Herpes Simplex Virus-1

ELISA for detection of HSV-1 envelope glycoprotein B (gB) was performed by infection of normal dermal fibroblast cells (NHDF, Clonetics) with HSV-1 (KOS) at a multiplicity of infection of 0.05 PFU/cell. Following virus adsorption, cells were washed and treated with growth media containing oligonucleotide. Oligonucleotides were tested in triplicate wells at four concentrations. Cells were fixed 48 hours postinfection and assayed for the presence of HSV-1 gB antigen by ELISA. Standard deviation were typically within 10%.

EXAMPLE 30

Inhibition of Herpes Simplex Virus-1 Activity by Phosphorothioate Oligonucleotide Sets A group of 65,536 unique 8-mers in 4 sets of 16,348 was prepared in accordance with Examples 3 and 6 and was screened for activity against human herpes simplex virus type 1 (HSV-1) in cell culture in accordance with the procedure described in Example 11. As illustrated in Table 4, antiviral activity was observed with increasing potency at each round of synthesis and screening, with no difficulty discerning the most active set (in bold) in each round.

TABLE 4

| | | | $IC_{50}$ (µM) when X = | | | |
|---|---|---|---|---|---|---|
| Round | Sequence* | Q** | A | C | G | T |
| 1 | NNNXNNNN | 16,348 | >100 | >100 | 70 | >100 |
| 2 | NNNGNNNX | 4,096 | >100 | >100 | 30 | >100 |
| 3 | NNNGNXNG | 1,024 | >100 | >100 | 15 | >100 |
| 4 | NXNGNGNG | 256 | 30 | 30 | 5 | 20 |
| 5 | XGNGNGNG | 64 | 20 | 20 | 1.5 | 20 |
| 6 | GGNGXGNG | 16 | 10 | 10 | 1.5 | 10 |
| 7 | GGXGGGNG | 4 | 1.3 | 1.3 | 0.5 | 1.3 |
| 8 | GGGGGGXG | 1 | 0.7 | 0.7 | 1.1 | 0.4 |

*where N is a mixture of A, C, G and T;
**where Q is set complexity.

The oligonucleotide set containing a fixed guanine had the most activity in every round of HSV screening except the last round, resulting in selection of a guanine at nearly all fixed positions.

EXAMPLE 31

Optimization of $G_4$ Core Containing 8-mer Oligonucleotide for HSV-1 Antiviral Activity To determine the optimal 8-mer containing a $G_4$ core, a oligonucleotide group was designed as shown in Table 5, using the oligonucleotide cassette GGGG.

TABLE 5

| Sequence* | Most Active X = | $IC_{50}$ (µM) |
|---|---|---|
| NNGGGGNX | A | 2.5 |
| NNGGGGXA | T | 1.1 |
| XNGGGGTA | G | 0.8 |
| GXGGGGTA | C | 0.8 |

*N is a mixture of A, G, T and C.

As shown in Table 5, optimization of the sequences surrounding the $G_4$ core produced a 3 fold increase in antiviral activity in four rounds of synthesis and screening, suggesting that although the $G_4$ core is the most important component of the activity, potency can be modulated by the flanking sequences.

EXAMPLE 32

Assay for Detection of Inhibition of Human Immunodeficiency Virus

An in vitro HIV infection assay was used to select inhibitors of HIV replication from combinatorial libraries. Buckheit et al., *Antiviral Res.* 1993, 21, 247. Human T-lymphoblastoid CEM cell line was maintained in an exponential growth phase in RPMI 1640 with 10% fetal calf serum, glutamine, and antibiotics. On the day of the assay, the cells were washed and counted by trypan blue exclusion. These cells (CEM-IIIB) were seeded in each well of a 96-well microtiter plate at $5 \times 10^3$ cells per well. Following the addition of cells to each well, the compounds were added at the indicated concentrations and serial half log dilutions. Infectious HIV-1$_{IIIB}$ was immediately added to each well at a multiplicity of infection determined to give complete cell killing at 6 days post-infection. Following 6 days of incubation at 37° C., an aliquot of supernatant was removed from each well prior to the addition of the tetrazolium dye XTT to each well. The XTT was metabolized to a formazan blue product by viable cells which was quantitatively measure spectrophotometrically with a Molecular Devices Vmax Plate Reader. The XTT assay measures protection from the HIV-induced cell killing as a result of the addition of test compounds. The supernatant aliquot was utilized to confirm the activities determined in the XTT assay. Reverse transcriptass assays and p24 ELISA were performed to measure the amount of HIV released from the infected cells. Protection from killing results in an increased optical density in the XTT assay and reduced levels of viral reverse transcriptass and p24 core protein.

EXAMPLE 33

Inhibition of Human Immunodeficiency Virus by Phosphorothioate Oligonucleotide Sets A group of 65,536 unique 8-mers in 4 sets of 16,348 each were prepared in accordance with Examples 3 and 6 and screened for activity in accordance with Example 32. The compound sets are described in Table 6. Table 6 sets forth the $IC_{50}$ (µM) for four oligonucleotide sets.

TABLE 6

| Set | Sequence* | $IC_{50}$ (µM) |
|---|---|---|
| A | NNNN A NNN | inactive |
| B | NNNN C NNN | inactive |
| C | NNNN G NNN | 5 |
| D | NNNN T NNN | inactive |

*where N is a mixture of A, C, G, and T.

Set C showed 50% inhibition of HIV-induced cytopathic effects at 5 µM, while the other compound sets were inactive at concentration up to 25 µM.

EXAMPLE 34

Assay for the Detection of Inhibition of Cytomegalovirus

Confluent monolayer cultures of human dermal fibroblasts were treated with oligonucleotide sets at the indicated concentrations in serum-free fibroblast growth media. After overnight incubation at 37° C., culture medium containing oligonucleotide was removed, cells were rinsed and human cytomegalovirus was added at a multiplicity of infection of 0.1 pfu/cell. After a 2 hour adsorption at 37° C., virus was removed and fresh fibroblast growth medium containing oligonucleotide sets at the indicated concentrations was added. Two days after infection, old culture medium was removed and replaced with fresh fibroblast growth medium containing oligonucleotide sets at the indicated concentrations. Six days after infection media was removed, and cells fixed by addition of 95% ethanol. HCMV antigen expression was quantitated using an enzyme linked immunoassay. Primary reactive antibody in the assay was a monoclonal antibody specific for a late HCMV viral protein. Detection was achieved using biotinylated goat anti-mouse IgG as secondary antibody followed by reaction with streptavidin conjugated B-galactosidase. Color was developed by addition of chlorophenol red B-D-galactopyranoside and absorbance at 575 nanometers measured using an ELISA plate reader. Results are expressed as percent of untreated control.

EXAMPLE 35

Inhibition of Cytomegalovirus by Phosphorothioate Oligonucleotide Sets

Figure 3:
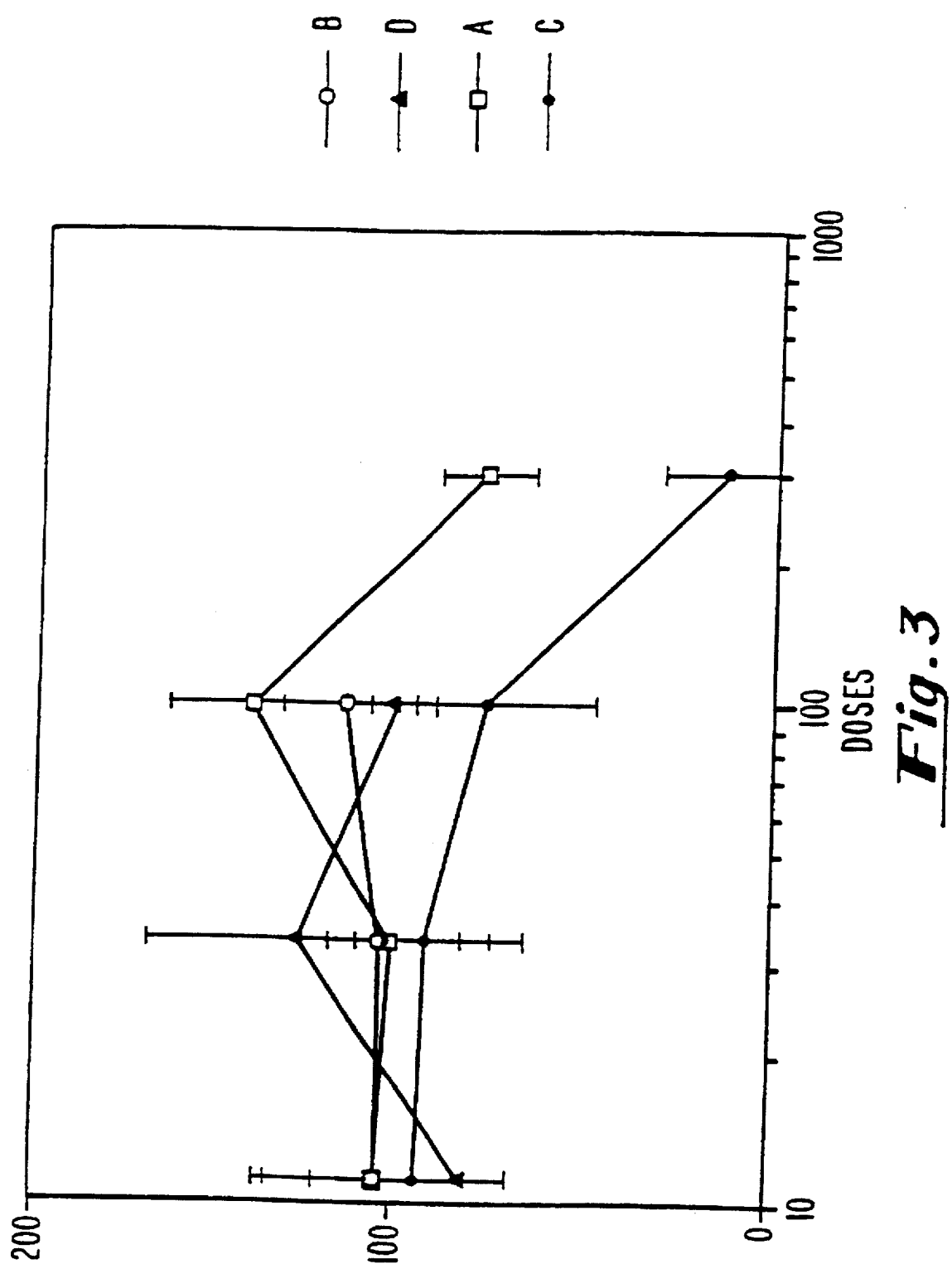
FIG. 3 is a schematic representation of inhibition of cytomegalovirus activity by four different oligonucleotide sets. Compound set C had the greatest activity against cytomegalovirus.

A group of 65,536 unique phosphorothioate 8-mers in 4 sets of 16,438 were prepared in accordance with Examples 3 and 6 and screened for activity against the human cytomegalovirus in accordance with Example 17. The compound sets A (NNNNANNN), B (NNNNGNNN), C(NNNNCNNN) and D (NNNNTNNN), where N is a mixture of A, G, C and T, were screened at a range of concentrations from 10 to 200 µM. The results shown in FIG. 3 show that compound set C had the greatest activity against cytomegalovirus, causing approximately 20% inhibition at a 100 µM dose and 90% inhibition at a 200 µM dose. Sets A, B and D exhibited minimal to no antiviral activity.

EXAMPLE 36

Assay to Detect Inhibition of Influenza A Virus

Vero cells were pretreated overnight with randomer sets by direct addition to the media at 10 µM and 100 µM concentrations. After overnight treatment cells were infected with influenza A/PR/8 at a MOI of 0.05. Following infection cells were incubated for 48 hours in the presence of oligonucleotide. After incubation cells were fixed with methanol and air dried. Monolayers were then assayed by ELISA for matrix protein. Primary antibody was a monoclonal antibody specific for matrix protein of influenza A virus (B020 Bioproducts for Science). Second antibody was goat anti-mouse IgG conjugated to alkaline phosphatase (BRL, Bethesda, Md.). Substrate was ATTO-PHOS reagent, JBL. Fluorescence was measured using a Millipore Cytofluor 2300 with excitation at 450 nM and emission read at 580 nM.

EXAMPLE 37

Inhibition of Influenza Virus by Phosphorothioate Oligonucleotide Sets

Figure 4:
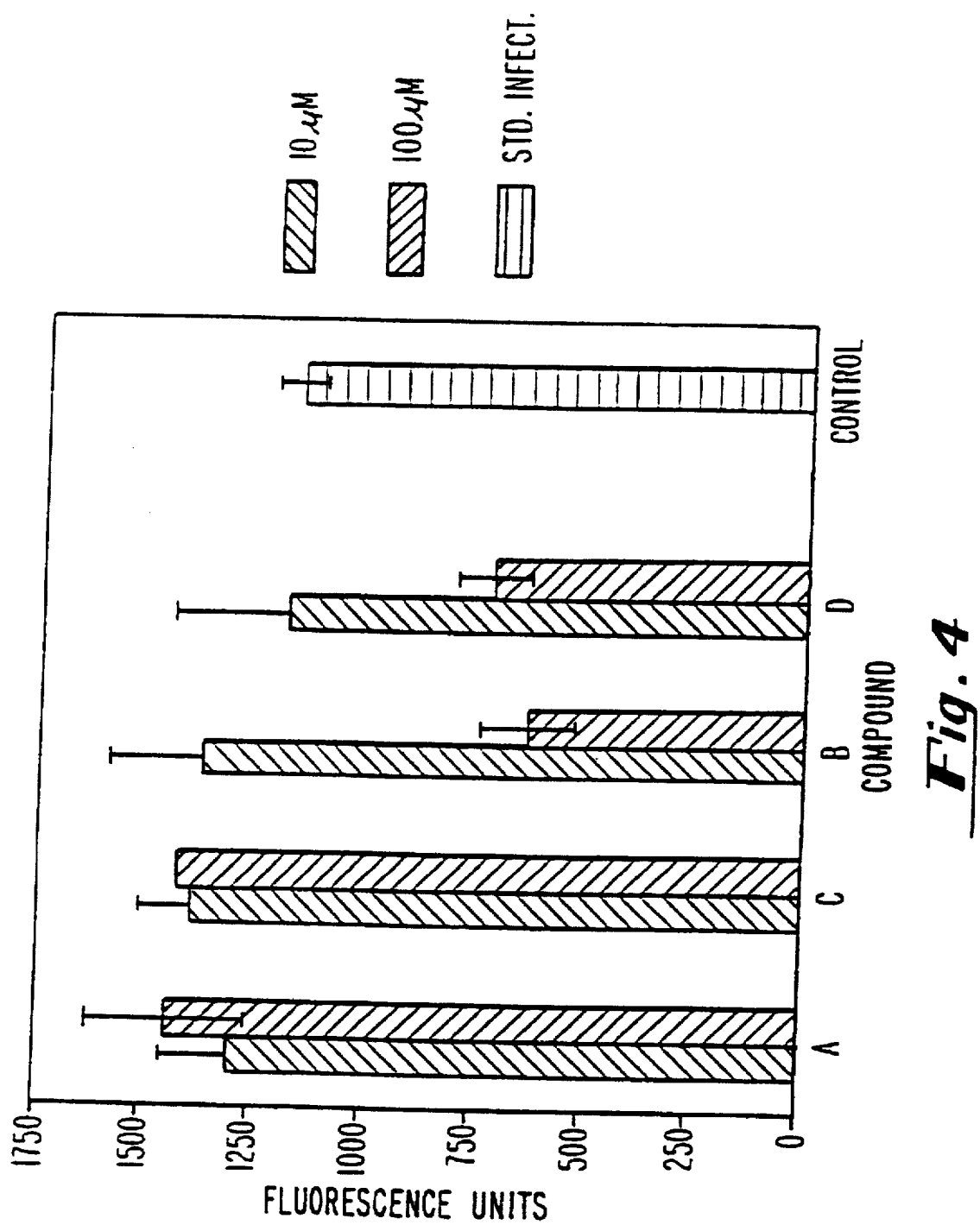
FIG. 4 is a schematic representation of inhibition of influenza virus activity caused by four different oligonucleotide sets at concentrations of 10 µM and 100 µM of oligonucleotide. Compound sets B and D had the greatest antiviral activities.

A group of 65,536 unique phosphorothioate 8-mers in 4 sets of 16,438 was prepared in accordance with Examples 3 and 6 and was screened for activity against the Influenza A virus as described in Example 19. The compound sets A (NNNNANNN), B (NNNNGNNN), C(NNNNCNNN) and D (NNNNTNNN), where N is a mixture of A, G, C and T, were screened at 10 µM and 100 µM. The results as shown in FIG. 4 show that sets C and D had the greatest antiviral activities, set C exhibited approximately 50% inhibition and set D exhibited approximately 35% inhibition of viral activity. A and B exhibited minimal activity.

Data are the arithmetic mean and standard error of triplicate data points of a single experiment.

EXAMPLE 38

Determination of Oligonucleotides which Induce Interferon

A phosphorothioate oligonucleotide group comprising 20 sets having the sequence N N N N X N N N where N is a mixture of adenine, guanine, cytosine, and thymidine and X is one of adenine, guanine, cytosine or thymidine is prepared in accordance with Examples 3 and 6. The sets are set forth in Table 7.

TABLE 7

| Set   | Modification      |
|-------|-------------------|
| 1–4   | 2'-deoxy (natural)|
| 5–8   | 2'-O-methyl       |
| 9–12  | 2'-O-propyl       |
| 13–16 | 2'-O-pentyl       |
| 17–20 | 2'-O-nonyl        |

An ELISA is performed to determine the set which is most effective to induce interferon. The nucleotide in the most effective set is fixed and sets having the fifth position fixed and the fourth position one of adenine, guanine, cytosine or thymidine is prepared. An ELISA is performed to determine the set which is most effective to induce interferon. The steps are repeated until all of the positions are determined.

EXAMPLE 39

Gel Shift Assay of Random Pyrene Oligonucleotide Sets Binding to HIV TAR Element The HIV TAR element is a structured RNA found on the 5'-end of all HIV transcripts. A gel shift was used to analyze the binding of four oligonucleotide sets to the HIV TAR element (illustrated in FIG. 5A). The target RNA has a three base bulge that is required for binding of the transcriptional activation protein tat. The oligonucleotides set forth in Table 8 were prepared in accordance with Examples 5 and 6, each containing a pyrene analog (indicated by A*).

TABLE 8

|       |                       | SEQ ID NO: |
|-------|-----------------------|------------|
| SET 1 | N N N A* N A N N N N  | 3          |
| SET 2 | N N N A* N C N N N N  | 4          |
| SET 3 | N N N A* N G N N N N  | 2          |
| SET 4 | N N N A* N U N N N N  | 5          |

Figures 5A, 5B, 6:
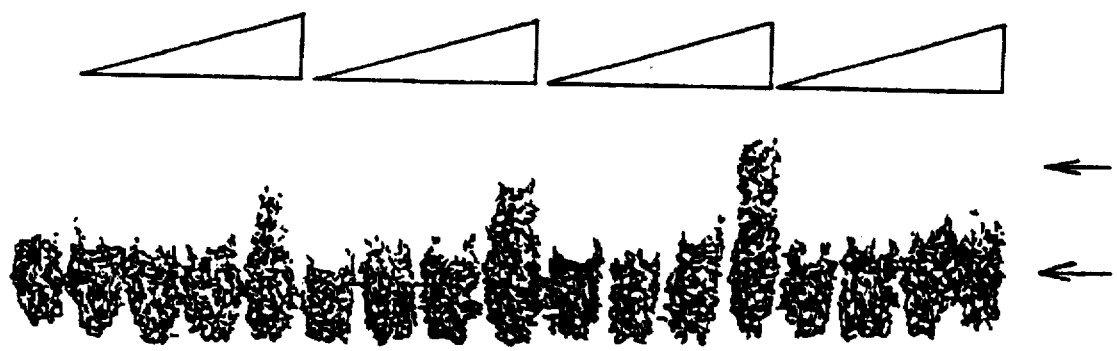
FIG. 5A is a schematic representation of the nucleotide sequence and secondary structure of the HIV TAR element (SEQ ID NO:20).
FIG. 5B is a representation of gel image showing binding affinity of four oligonucleotide sets for the HIV TAR element at four different oligonucleotide concentrations. The oligonucleotide set NNNA*NGNNNN (SEQ ID NO:2) had the greatest binding affinity.
FIG. 6 is a schematic representation of the nucleotide sequence and secondary structure of the HIV gag-pol stem loop (SEQ ID NO:21).

The assay used a 15 pM concentration of the radioactively labeled target and 0.1, 1, 10, and 100 µM concentrations of each set. Binding of molecules from the set to the target resulted in a slower mobility complex. Set 3 bound best to TAR as illustrated in FIG. 5B wherein 100 µM of the oligonucleotide set caused a shift of approximately 50% of the target. 100 µm of the oligonucleotide set 2 caused a shift of approximately 25% of the target. Sets 1 and 4 caused minimal shift of the target. The sixth position will be fixed as a G and another position unrandomized in the second round of synthesis and assays.

EXAMPLE 40

Random Oligonucleotide Set Binding to HIV gag-pol Triple Strand

Binding to double stranded DNA or RNA is possible by formation of a three stranded complex, with the incoming third strand binding in the major groove of the duplex RNA or DNA. FIG. 6 illustrates a double stranded RNA structure from HIV known as the gag-pol stem loop (Vickers and Ecker, Nucleic Acids Research). One of the limitations in the design of triple strand interactions is the need to have a long stretch of homopurines as a target. The 3' (right) side of the gag-pol stem loop is homopurine except for a pair of cytosines near the bottom of the stem. To determine the best oligonucleotide to bind to the gag-pol stem loop, a group of RNA oligonucleotide sets was designed to bind to the purine-rich strand of the gag-pol stem-loop by Hoogstein base pairing and prepared in accordance with Examples 2 and 6. At the position of the two cytosines the sequence was randomized to provide the sequences set forth in Table 9. Binding to the gag-pol stemloop was measured by gel shift analysis as previously described in Example 8 with the following modifications: the radiolabeled gag-pol RNA was incubated with the oligonucleotide in 100 mM NaCl, 25 mM TRIS acetate (pH 5), 2 mM $MgCl_2$, 1 mM spermidine. The gel was 15% acrylamide with 50 mM NaCl and 2 mM $MgCl_2$ added to the running buffer.

The results in Table 9 show that in round 1 the oligonucleotide set CCCUUCCCNUC(SEQ ID NO: 8) had the greatest affinity for the target with a $K_D$ of 50. In the second round the C was fixed in the eighth position and the ninth position was determined. The oligonucleotide CCCUUCCCCUC(SEQ ID NO: 12) had the greatest affinity for the target in the ninth round with a $K_D$ of 1. Thus, although the molecular nature of the interaction between the oligomer and target need not be known in order to practice the methods of the invention, a known interaction such as triple strand-binding can be optimized.

TABLE 9

| Set | Sequence | $K_D$ (µM) | SEQ ID NO: |
|---|---|---|---|
| Round 1 | | | |
| $A_1$ | CCCUUCCANUC | >100 | 6 |
| $B_1$ | CCCUUCCGNUC | >100 | 7 |
| $C_1$ | CCCUUCCCNUC | 50 | 8 |
| $D_1$ | CCCUUCCUNUC | 100 | 9 |
| Round 2 | | | |
| $A_2$ | CCCUUCCCAUC | 10 | 10 |
| $B_2$ | CCCUUCCCGUC | 10 | 11 |
| $C_2$ | CCCUUCCCCUC | 1 | 12 |
| $D_2$ | CCCUUCCCUUC | 10 | 13 |

EXAMPLE 41

Random Oligonucleotide Binding to Transcription Factors

A radiolabeled oligonucleotide group was prepared having the sequence NNGGGGNX wherein N is a mixture of A, G, T, and C and X is one of A, G, T or C as described in Examples 3, 6 and 7. The group was screened for binding to the HIV tat protein, which is a transcription factor produced by the virus as described in Example 22. Binding activity was observed.

EXAMPLE 42

Random 2'-O-Methyl Oligonucleotide Binding to Endothelin-1

Receptor and radiolabeled ligand were supplied in a kit obtained from DuPont/NEN. Assays were performed according to the manufacturer's instructions. A random 2'-O-methyl group was prepared in accordance with Examples 4 and 6 to provide four sets having the sequences GCGNNNANNNNNNCGC (SEQ ID NO: 14); GCGNNNGNNNNNNCGC (SEQ ID NO:15); GCGNNNCNNNNNNCGC (SEQ ID NO:16); GCGNNNUNNNNNNCGC (SEQ ID NO: 17) where N is a mixture of A, G, C, and U. Each set was diluted to 100 µM in an assay buffer provided in the kit, then incubated with the receptor and ligand as per the manufacturer's protocol. Following the incubation, ligand-bound receptor was separated from unbound by vacuum filtration through glass filters. The bound ligand was then eluted from the filter in scintillation fluid and counted in a scintillation counter. Receptor and ligand were incubated with an excess of unlabeled ligand in order to establish the level of non-specific binding (NSB) to the filters and with no oligonucleotide set (zero) to establish the level of complete binding.

The results shown in Table 10 indicate that set B was most active against Endothelin-1.

TABLE 10

| | CPM | NET CPM | % I |
|---|---|---|---|
| NSB | 284 | — | — |
| zero | 1421 | 1140 | 100 |
| A | 1223 | 939 | 82 |
| B | 1200 | 916 | 80 |
| C | 1347 | 1063 | 93 |
| D | 1330 | 1046 | 92 |

EXAMPLE 43

Random 2'-O-Methyl Oligonucleotide Binding to Leukotriene B4

Receptor and radiolabeled ligand were supplied in a kit obtained from DuPont/NEN. Assays were performed according to the manufacturer's instructions. A random 2'-O-methyl group was prepared in accordance with Examples 4 and 6 to provide four sets having the sequences GCGNNNANNNNNNCGC (SEQ ID NO: 14); GCGNNNGNNNNNNCGC (SEQ ID NO:15); GCGNNNCNNNNNNCGC (SEQ ID NO:16); GCGNNNUNNNNNNCGC (SEQ ID NO: 17) where N is any of A, G, C or U. Each set was diluted to 100 µM in an assay buffer provided in the kit, then incubated with the receptor and ligand as per the manufacturer's protocol. Following the incubation, ligand-bound receptor was separated from unbound by vacuum filtration through glass filters. The bound ligand was then eluted from the filter in scintillation fluid and counted in a scintillation counter. Receptor and ligand were incubated with an excess of unlabeled ligand in order to establish the level of non-specific binding (NSB) to the filters and with no oligonucleotide set (zero) to establish the level of complete binding. The results shown in Table 11 indicate that set D was most active against leukotriene B4.

TABLE 11

| | CPM | NET CPM | % I |
|---|---|---|---|
| NSB | 383 | — | — |
| zero | 1063 | 680 | 100 |
| A | 989 | 606 | 89 |
| B | 953 | 570 | 84 |
| C | 900 | 517 | 76 |
| D | 894 | 511 | 75 |

EXAMPLE 44

Phosphorothioate and 2'-O-Methyl Oligonucleotide Binding to the Vital Receptor CD4

Two groups of oligonucleotides were prepared. A phosphorothioate oligonucleotide group was prepared in accordance with Examples 3 and 6. A 2'-O-methyl oligonucleotide group was prepared in accordance with Examples 4 and 6. Both groups have the sequence NNNNTNNNN where N is a mixture of A, C, G, and T.

Figure 7:
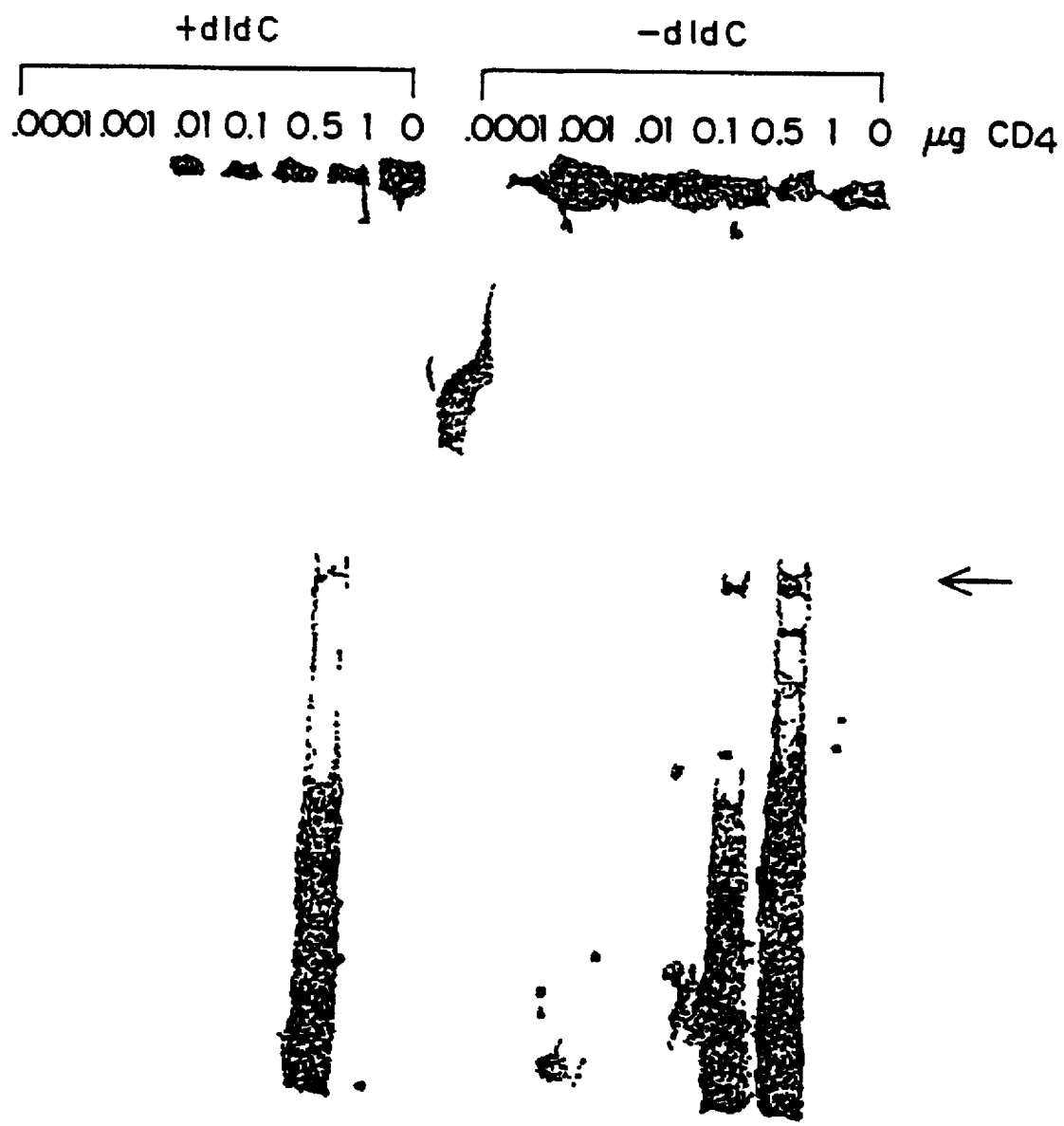
FIG. 7 is a representation of gel image showing the binding affinity of 100 pmoles of a phosphorothioate oligonucleotide set having the sequence NNNNTNNNN for the protein CD4 in the presence and absence of a competitor, dIdC. 100 pmoles exhibited binding which was visible at 0.5 and 1 µg CD4.

100 pmoles of each group of random oligonucleotides is 5' end labeled to high specific activity with [$\gamma$-$^{32}$P] ATP and T4 polynucleotide kinase. Each labeled group is reacted with the protein CD4 at room temperature in a buffer consisting of 100 mM KCl, 1.5 mM $MgCl_2$, 0.2 mM EDTA, 10% glycerol, 1 mM DTT, and 20 mM HEPES (pH 7.9). Poly dI·dC is added as indicated as a non-specific competitor. After 1 hour protein bound oligonucleotide is separated from unbound by electrophoresis on a 6% native acrylamide gel in 1× TBE buffer. The results of the phosphorothioate oligonucleotide assay is shown in FIG. 7 and indicates binding of the oligonucleotide to the protein (at the arrow). No binding was detected by the 2'-O-methyl set. Binding was observed with the phosphorothioate pool against the tat protein.

EXAMPLE 45

Preparation of Random Groups of Polypeptides and Assay for Binding Thereof

Polypeptides may be used in the practice of this invention. Monomer amino acids are easily oligomerized into peptides using the appropriate precursor chemicals and instruments available to those skilled in the art, such as those that can be purchased from Applied Biosystems.

The first round of synthesis is as shown in Table 12:

TABLE 12

| Position | 1 | 2 | 3 | 4 | 5 | 6 | 7 | 8 | 9 |
|---|---|---|---|---|---|---|---|---|---|
| Set 1 | X | X | X | X | B | X | X | X | X |
| Set 2 | X | X | X | X | A | X | X | X | X |
| Set 3 | X | X | X | X | W | X | X | X | X |
| Set 4 | X | X | X | X | L | X | X | X | X | where A is defined as an acidic amino acid, B is defined as a basic amino acid, W is defined as a neutral amino acid, L is defined as a lipophilic amino acid, and X is defined as any amino acid from the above identified group.

Each of the above sets is tested for inhibition of cell adhesion using a cell culture assay in which the ICAM-1 mediated binding of cells is measured as described. Dustin and Springer, *J. Cell Biol.* 1988, 107, 321. The set showing greatest inhibition of cell adhesion at the lowest polypeptide concentration is selected.

The protocol is repeated, retaining the selected amino acid at position 5, and sequentially testing each remaining position to reach an optimal binding sequence.

EXAMPLE 46

Figure 8:
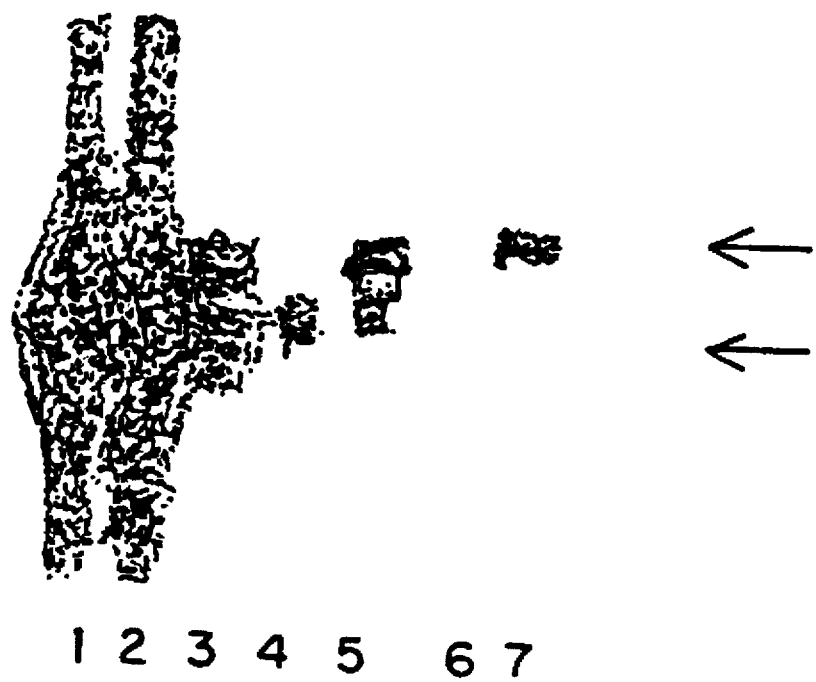
FIG. 8 is a representation of gel image showing selection of an oligonucleotide with the highest affinity for a biotinylated target oligonucleotide. The "winner" sequence (top arrow) was evident through three rounds of the procedure. Lane 1 is the input material diluted 1:10. Lane 2 is the supernatant diluted 1:10. Lane 3 is the bound material. Lanes 4 and 5 are the supernatant (1:10 dilution) and bound material of round 2, respectively. Lanes 6 and 7 are the supernatant (1:10 dilution) and bound material of round 3, respectively. The top arrow indicates "winner" material. Randomer library material migrates to the position indicated by the bottom arrow.

Identification of Oligonucleotide Sequence Using Streptavidin Capture of Biotinylated Target A target oligonucleotide (0.2 µM) having the sequence 3'dBAB AGA CGT CTT GCG 5' (SEQ ID NO: 18) wherein B is biotin, was incubated for 30 minutes at room temperature with 10 µM of a radiolabeled 2'-O-methyl oligonucleotide group prepared in accordance with Examples 4, 6 and 7 having the sequence NNN NCN CNN wherein N is any of adenine, cytosine, thymidine or guanine, and 0.1 µM of a radioactively labeled oligonucleotide complementary to the target (dTCTGCAGAACGC; SEQ ID NO: 19). The target oligonucleotide and any bound radioactively labeled oligonucleotide was captured on streptavidin-coated magnasphere beads (Promega), the beads were washed, and supernatant removed. The captured radioactively labeled oligonucleotide was removed from the beads and run on a polyacrylamide gel. FIG. 8 sets forth a sample gel which indicates that a "winner" can be separated from an excess of random sequence oligonucleotides. The procedure was repeated. In lane 1 was run a 1:10 dilution of the original solution prior to capture. Lane 2 is the supernatant diluted 1:10. Lane 3 is the bound material from the first round. A band of "winner" sequence is apparent, migrating to the first arrow. Lanes 4 and 5 are the supernatant (1:10 dilution) and bound material from the second round, respectively. The second round results in a "winner" band of greater purity. Lanes 6 and 7 are the supernatant (1:10 dilution) and bound material from the third round, respectively. The supernatant does not contain any radiolabeled oligonucleotides. The third round results in a "winner" band with little to no non-specific oligonucleotide.

EXAMPLE 47

Identification of a Protein Target

A target protein may be identified based upon the fact that proteins bind to free aldehyde groups while nucleic acids do not. Thus, a sampling of proteins which have been identified as potential targets may be bound to solid supports having free aldehyde groups such as nitrocellulose filters. For example, up to 96 proteins may be bound in individual wells of a 96-well nitrocellulose filter manifold.

A group of oligonucleotides having the sequence NNNNNNNN wherein N is a mixture of adenine, guanine, thymidine, and cytosine is prepared in accordance with Examples 3 and 6. The group is labeled using $[\gamma^{-32}P]$ ATP and T4 polynucleotide kinase.

In individual wells of a 96-well nitrocellulose filter manifold, the following proteins are incubated in a solution of phosphate buffer saline: plasminogen activator $A_2$, tumor necrosis factor α, tumor necrosis factor β and gp120. Phosphate buffer saline only is added to a control well. The filter is washed. An aliquot of the labeled group of oligonucleotides is added to each well and incubated at room temperature for 10 minutes. The filter is washed and the radioactivity over background in each well is counted to determine whether binding of the oligonucleotide to the protein occurred.

EXAMPLE 48

Determination of Phosphorothioate Oligonucleotide Having Binding Affinity for Nitrocellulose Bound Proteins An oligonucleotide analog group comprising four sets of oligonucleotides eight positions in length is prepared in accordance with Examples 3 and 6 and each set is tested for binding against the nitrocellulose-bound proteins identified in accordance with Example 47. The set having the highest affinity for each protein, as indicated by counts per well is the "winner set" for each protein. Results of the first round are as set forth in Table 13.

TABLE 13

| Position | 1 | 2 | 3 | 4 | 5 | 6 | 7 | 8 | Protein winner |
|---|---|---|---|---|---|---|---|---|---|
| Set 1 | N | N | N | N | A | N | N | N | plasminogen activator $A_2$, tumor necrosis factor α |
| Set 2 | N | N | N | N | G | N | N | N | no winner |
| Set 3 | N | N | N | N | C | N | N | N | gp120 |
| Set 4 | N | N | N | N | T | N | N | N | tumor necrosis factor β |

The filter is washed and wells counted. In a second round, the A is fixed in the fifth position and the sets (NNNAANNN), (NNNGANNN), (NNNCANNN), and (NNNTANNN) are prepared for testing in the wells containing plasminogen activator A2 and tumor necrosis factor α. Similarly, sets in which the C is fixed in the 5th position or a T is fixed in the 5th position are prepared for testing in the gp120 and tumor necrosis factor β wells, respectively. By the eight round, "winner" sequences for all four target proteins are determined.

EXAMPLE 49

Determination of an Oligonucleotide Having Binding Affinity for a Target Protein using Subfractionated Sets of Oligonucleotides An oligonucleotide analog group comprising four sets of oligonucleotides eight positions in length is prepared in accordance with Examples 3 and 6 wherein each of the sets has a different one of adenine, guanine, thymidine and cytosine in the 5th position, and the rest of the positions are randomized to provide the group: NNNNANNN, NNNNGNNN, NNNNTNNN, and NNNNCNNN. Each set is subfractionated by charge with an anion exchange column. Each subfraction is tested for affinity for the target protein by gel shift assay. The subfraction from the set having an adenine in the 5th position has the highest binding affinity. In a further round, the 5th position is fixed to contain an adenine in the 5th position, and each set has a different nucleotide in the fourth position to provide the group NNNAANNN, NNNTANNN, NNNGANNN, and NNNCANNN. The sets are again subfractionated by charge with an anion exchange column and the subfractions are tested for affinity for the target protein by gel shift assay. The steps are repeated until each position is determined.

EXAMPLE 50

PLA$_2$ assay

Phospholipase A$_2$ (PLA$_2$) enzymes are responsible for the hydrolysis of the sn-2 linkage of membrane phospholipids. PLA2-catalyzed reaction is the rate-limiting step in the release of a number of pro-inflammatory mediators, and type II PLA$_2$ is implicated in the pathogenesis of several human inflammatory diseases. Library subsets of oligomers comprising phosphodiester linkages (shown in Table 14) were screened for inhibition of the activity of type II PLA$_2$ and a unique inhibitor was identified.

The oligomer libraries were screened for inhibition of PLA$_2$ in an assay using E. coli cells labeled with $^3$H-oleic acid as the substrate. Franson et al., J. Lipid Res. 1974, 15, 380; and Davidson et al., J. Biol. Chem. 1987, 262, 1698. Type II PLA$_2$ (originally isolated from synovial fluid), expressed in a baculovirus system and partially purified, serves as a source of the enzyme. A series of dilutions (in water) of each of the oligomeric pools was made: 10 μL of each oligomer was incubated for 5 minutes at room temperature with a mixture of 10 μL of PLA$_2$, 20 μL 5×PLA$_2$, buffer (500 mM Tris, pH 7.0–7.5, 5 mM CaCl2) and 50 μL water. Each of the oligomer samples was run in duplicate. At this point, 10 μL of $^3$H-labeled E. coli cells was added. This mixture was incubated at 37° C. for 15 minutes. The enzymatic reaction was halted with the addition of 50 μL of 2M HCl and 50 μL of fatty acid-free BSA (20 mg/mL PBS), vortexed for 5 seconds and centrifuged at high speed for 5 minutes. A 165 μL portion of each supernatant was then put into a scintillation vial containing 6 mL of scintillant (Scintiverse) and cpms were measured in a Beckman Liquid Scintillation Counter. As a control, a reaction without oligomer was run alongside the other reactions as well as a baseline reaction containing neither oligomer nor PLA$_2$ enzyme. Cpms were corrected for by subtracting the baseline from each reaction data point. The results are shown in Table 14, and the structures of the monomer units (X) are shown in Scheme 1.

TABLE 14

Identification of active oligomer, comprising phosphodiester linkages, using SURF.™

| | | IC$_{50}$ (μM) for X = | | | | | |
|---|---|---|---|---|---|---|---|
| Round | Sequence | dG | dT | mU | noC | pG | CB |
| 1 | XNNNdT | >100 | >100 | >100 | <u>30</u> | 60 | >100 |
| 2 | (noC)XNNdT | >100 | >100 | >100 | <u>20</u> | 35 | >100 |
| 3 | (noC)$_2$XNdT | <u>10</u> | >50 | >50 | 20 | 15 | >50 |
| 4 | (noC)$_2$(dG)XdT | 5 | <u>2</u> | 5 | 8 | 5 | >10 |

The first two rounds were useful for determining the first two monomer units, i.e. noC, of the oligomer. The next two positions were determined to be dG and dT, in that order, and the unique oligomer with the greatest activity was identified to be (noC) (noC) (dG) (dT) (dT) with an IC$_{50}$ of 2 μM.

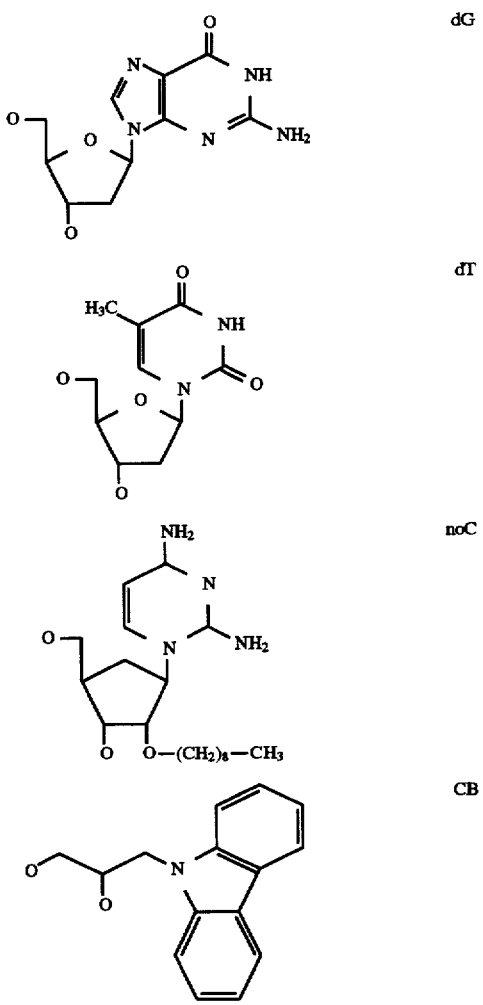

SCHEME 1

-continued
SCHEME 1

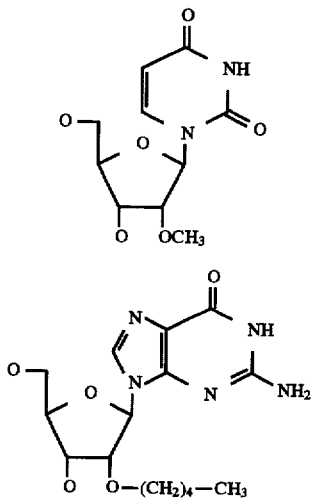

EXAMPLE 51

Leukotriene B₄ assay

Leukotriene B₄ (LTB₄) has been implicated in a variety of human inflammatory diseases, and its pharmacological effects are mediated via its interaction with specific surface cell receptors. Library subsets of oligomers comprising phosphodiester linkages were screened for competitive inhibition of radiolabeled LTB₄ binding to a receptor preparation, and are shown in Table 15.

A Nenquest™ Drug Discovery System Kit (NEN Research Products, Boston, Mass.) was used to select an inhibitor of the interaction of Leukotriene B₄ (LTB₄) with receptors on a preparation of guinea pig spleen membrane. [³H] Leukotriene B₄ reagent was prepared by adding 5 mL of ligand diluent (phosphate buffer containing NaCl, MgCl₂, EDTA and Bacitracin, pH 7.2) to 0.25 mL of the radioligand. The receptor preparation was made by thawing the concentrate, adding 35 mL of ligand diluent and swirling gently in order to resuspend the receptor homogenously. Reagents were kept on ice during the course of the experiment, and the remaining portions were stored at -20° C.

The library subsets were diluted to 5 µM, 50 µM and 500 µM in phosphate buffer (1×PBS, 0.1% azide and 0.1% BSA, pH 7.2), yielding final test concentrations of 0.5 µM, 5 µM and 50 µM, respectively. Samples were assayed in duplicate. [³H] LTB₄ (25 µL) was added to 25 µL of either appropriately diluted standard (unlabeled LTB₄) or library subset. The receptor suspension (0.2 mL) was added to each tube. Samples were incubated at 4° C. for 2 hours. Controls included [³H] LTB₄ without receptor suspension (total count vials), and sample of ligand and receptor without library molecules (standard).

After the incubation period, the samples were filtered through GF/B paper that had been previously rinsed with cold saline. The contents of each tube were aspirated onto the filter paper to remove unbound ligand from the membrane preparation, and the tubes washed (2×4 mL) with cold saline. The filter paper was removed from the filtration unit and the filter disks were placed in appropriate vials for scintillation counting. Fluor was added, and the vials shaken and allowed to stand at room temperature for 2 to 3 hours prior to counting. The counts/minute (cpm) obtained for each sample were subtracted from those obtained from the total count vials to determine the net cpm for each sample. The degree of inhibition of binding for each library subset was determined relative to the standard (sample of ligand and receptor without library molecules). The results are shown in Table 15 and the structures of the monomer units (X) are shown in Scheme 2.

TABLE 15

Identification of active oligomer, comprising phosphodiester linkages, using SURF.™

| | | IC₅₀ (µM) for X = | | | | | |
|---|---|---|---|---|---|---|---|
| Round | Sequence | dG | dT | BT1 | BT2 | IM | CB |
| 1 | XNNNdT | >50 | >50 | >50 | >50 | >50 | <u>40</u> |
| 2 | (CB)XNNdT | >10 | >10 | 9 | >10 | >10 | <u>6</u> |
| 3 | (CB)₂XNdT | 1.9 | >5 | <u>1.7</u> | 1.9 | >5 | 2.2 |
| 4 | (CB)₂(BT1)XdT | 0.92 | >1 | 0.76 | >1 | 0.90 | <u>0.68</u> |

In the initial round of screening, the subset with CB in the first position, i.e. (CB)NNNdT, showed greatest activity. In the second round, subset (CB) (CB)NNdT was most active, and the activity increased from an IC₅₀ of 40 µM in round 1 to 6 µM in round 2, an approximately 6-fold increase in activity. Assay of round 3 subsets resulted in the identification of four subsets with similar activity, approximately 2 µM. In this round, the preferred monomer unit was BT1. In the final round of SURF,™ several pools showed activity, and (CB) (CB) (BT1) (CB)dT was identified as the most active oligomer in this assay with an IC₅₀ of 0.68 µM.

SCHEME 2

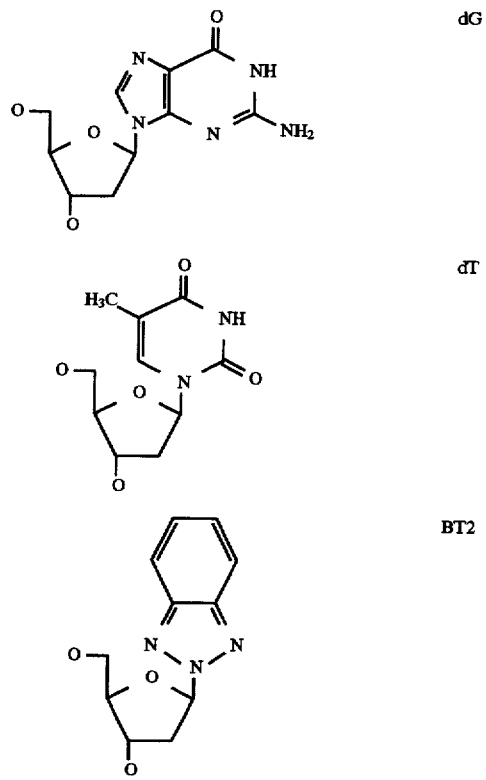

-continued
SCHEME 2

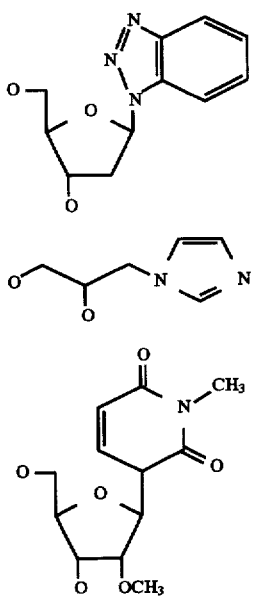

BT1

IM mmU

In order to identify the minimum active pharmacophore, a series of truncated oligomers based upon the active sequence identified were synthesized and tested for inhibition of $LTB_4$ binding. The smallest oligomer with good activity is (CB) (CB)(BT1), with an $IC_{50}$ of 3.0 µM. Two tandem carbazoles (CB) were required for best activity. Juxtaposition of BT1 between the two carbazoles reduced the activity significantly ($IC_{50}$=6.4 µM), indicating sequence specificity.

EXAMPLE 52

Synthesis of 1-(2'-deoxy-β-D-erythro-pentofuranosyl)-pyrrolo[4,5-d]pyridazin-4(5H),7(6H)-dione Diethyl pyrrole-3,4-dicarboxylate (10 g, 47.39 mmol) was heated to reflux with hydrazine monohydrate (5 mL) in ethanol (50 mL) for 24 hours. After this time, the pale yellow precipitate formed was filtered, washed with methanol (2×20 mL), air dried, resuspended in anhydrous hydrazine (20 mL), and refluxed at 140° C. for 12 hours. The clear solution was concentrated under reduced pressure. The residue was dissolved in boiling water (70 mL), acidified (pH 4) with concentrated HCl and filtered. The crystalline solid was washed with cold water (2×25 mL), ethanol (2×20 mL) and ether (20 mL), and air dried to furnish 6.06 g (84%) of pyrrolo[4,5-d]pyridazin-4(5H),7(6H)-dione. To this product (6.04 g, 40 mmol) is added hexamethyldisilazane (HMDS, 15 mL) and chlorotrimethylsilane (TMSCl, 0.5 mL), and refluxed at 150° C. for 1 hour. Excess HMDS/TMSCl is removed under vacuum and the residue dried. A mixture of this silylated product and 2-deoxy-3,5-di-O-p-toluoyl-α-D-erythro-pentofuranosyl chloride is anhydrous chloroform is stirred at room temperature under argon. CuI is added to the solution and the slurry stirred at room temperature for 3 hours. The reaction is quenched by the addition of a saturated solution of soldium bicarbonate, stirred for 15 minutes and filtered through celite. The chloroform layer is separated, washed with with saturated NaCl solution, dried with magnesium sulfate and concentrated under reduced pressure. The residue is purified by silica gel column chromatography and eluted with ethyl acetate/hexanes (1:1). The product so obtained is dissolved in methanol, and sodium methoxide is added. The reaction mixture is stirred at room temperature, neutralized with Dowex-50H$^+$ after 1 hour and filtered. The resin is washed with methanol and the combined filtrates concentrated under reduced pressure. The residue is dissolved in water, washed with chloroform and the aqueous layer freeze dried to afford the title compound.

What is claimed is:

1. A method for determining an oligonucleotide having an assayable activity for a target molecule comprising the steps of:

(a) preparing a group of sets of oligonucleotides of substantially the same length, each oligonucleotide comprising at least three nucleotide, by:
(i) defining a common position in the oligonucleotides of the sets, and
(ii) synthesizing said sets of oligonucleotides such that each set has a different nucleotide in said common position, the nucleotides which are not in said common position being randomized;

(b) assaying each of the sets for activity against the target molecule;

(c) selecting the set having the highest activity;

(d) preparing a further group of sets of oligonucleotides of said substantially same length, each of the sets of said further group having in the previously defined common position the nucleotide appearing in that position in the set selected in step (c), and having in an additional defined common position a different nucleotide, the nucleotides in the positions of the oligonucleotides which are not in a defined common position being randomized;

(e) assaying each of the sets of said further group for said assayable activity;

(f) selecting the set of said further group having the highest assayable activity; and (g) repeating steps (d) through (f) until an oligonucleotide having said assayable activity for said target molecule is determined.

2. The method of claim 1 further comprising the steps of:

(h) selecting an oligonucleotide of step (g) with the highest assayable activity;

(i) preparing additional oligonucleotides, each additional oligonucleotide differing from the oligonucleotide of step (h) by at least one nucleotide which has been added, deleted, or substituted by a different nucleotide;

(j) assaying said additional oligonucleotides for said assayable activity; and (k) selecting the oligonucleotide of said additional oligonucleotides having the highest assayable activity.

3. The method of claim 3 wherein steps (i) through (k) are performed iteratively until no additional oligonucleotides having an increase in said assayable activity is identified.

4. The method of claim 1 wherein said oligonucleotide is a cyclic oligonucleotide.

5. The method of claim 1 wherein said oligonucleotide is from 3 to 20 nucleotides in length.

6. The method of claim 1 wherein said oligonucleotide is labeled with a detectable label.

7. The method of claim 1 wherein said assaying is by gel shift assay, streptavidin capture of biotinylated target, filter binding assay or affinity chromatography.

8. The method of claim 1 wherein the oligonucleotide is sterically constrained.

9. The method of claim 1 wherein said assayable activity is binding activity for a target molecule.

10. The method of claim 9 wherein the target molecule is a nucleic acid.

11. The method of claim 9 wherein said target molecule is a carbohydrate.

12. The method of claim 9 wherein said target molecule is a protein.

13. The method of claim 9 wherein said target molecule is a glycoprotein.

14. The method of claim 9 wherein the target molecule is an immunoglobulin, receptor, receptor binding ligand, antigen, enzyme, or transcription factor.

15. The method of claim 9 wherein the target molecule is a phospholipase, tumor necrosis factor, endotoxin, interleukin, leukotriene, plasminogen activator, protein kinase, cell adhesion molecule, lipoxygenase, hydrolase, transacylase, or transcription factor.

16. The method of claim 9 wherein the target molecule is derived from Candida, papilloma virus, Epstein-Barr virus, rhinovirus, hepatitis virus, human immunodeficiency virus, herpes simplex virus, influenza virus or cytomegalovirus.

17. The method of claim 9 wherein the target molecule is an RNA molecule or fragment thereof.

18. The method of claim 16 wherein the target molecule is the TAR element of human immunodeficiency virus.

19. The method of claim 16 wherein the target molecule is the gag-pol stem loop of human immunodeficiency virus.

20. The method of claim 16 wherein the target molecule is the 47-base pair stem loop of ras.

21. The method of claim 15 wherein the target molecule is endothelin-1.

22. The method of claim 15 wherein the target molecule is leukotriene B-4.

23. The method of claim 16 wherein the target molecule is human immunodeficiency virus gp120.

24. The method of claim 22 wherein the target molecule is human immunodeficiency virus tat protein.

25. The method of claim 1 wherein the assayable activity is catalytic activity.

26. The method of claim 1 wherein the assayable activity is induction of cellular production of interferon.

27. A method for determining an oligonucleotide having an assayable activity for a target molecule comprising the steps of:

(a) binding a group of target molecules to a solid support;

(b) incubating the solid support with a group of oligonucleotides nucleotides labeled with a detectable label having all positions randomized, under binding conditions;

(c) detecting the presence or absence of binding wherein binding of an oligonucleotide indicates activity of the oligonucleotide for one or more target molecules, thereby identifying selected target molecules;

(d) preparing a group of sets of oligonucleotides of substantially the same length, each oligonucleotide comprising at least three nucleotides, by:
  (i) defining a common position in the oligonucleotides of the sets, and
  (ii) synthesizing said sets of oligonucleotides such that each set has a different nucleotide in said common position, the nucleotides which are not in said common position being randomized;

(e) assaying each of the sets for activity against said selected target molecules;

(f) selecting the set having the highest activity;

(g) preparing a further group of sets of oligonucleotides of said substantially same length, each of the sets of said further group having in the previously defined common position the nucleotide appearing in that position in the set selected in step (f), and having in an additional defined common position a different nucleotide, the nucleotides in the positions of the oligonucleotides which are not in a defined common position being randomized;

(h) assaying each of the sets of said further group for said assayable activity for said selected target molecules;

(i) selecting the set of said further group having the highest activity; and (j) repeating steps (g) through (i) until an oligonucleotide having an assayable activity for a target molecule is determined.

28. The method of claim 27 wherein said oligonucleotide is a cyclic oligonucleotide.

29. A method for determining an oligonucleotide cassette having an assayable activity for a target molecule comprising the steps of:

(a) preparing a group of sets of oligonucleotides of substantially the same length, each oligonucleotide comprising at least three nucleotides, by:
  (i) defining a common position in the oligonucleotides of the sets, and
  (ii) synthesizing said sets of oligonucleotides such that each set has a different nucleotide in said common position, the nucleotides which are not in said common position being randomized;
(b) assaying each of the sets for activity against the target molecule;
(c) selecting the set having the highest activity;
(d) preparing a further group of sets of oligonucleotides of said substantially same length, each of the sets of said further group having in the previously defined common position the nucleotide appearing in that position in the set selected in step (c), each set of said further group of sets having a different nucleotide in an additional defined common position, the nucleotides in the positions of the oligonucleotides which are not in a defined common position being randomized;
(e) assaying each of the sets of said further group for specific activity for the target molecule;
(f) selecting the set of said further group having the highest activity; and
(g) repeating steps (d) through (f) until an oligonucleotide cassette having said assayable activity for said target molecule is determined.

30. The method of claim 29 wherein said oligonucleotide is a cyclic oligonucleotide.

31. A method for determining an oligonucleotide having an assayable activity for a target molecule comprising the steps of:
(a) preparing a group of sets of oligonucleotides of substantially the same length, each oligonucleotide comprising at least one predefined oligonucleotide cassette and at least one flanking region by:
(i) defining a common position in said flanking region of the oligonucleotides of the sets, and
(ii) synthesizing said sets of oligonucleotides such that each set has a different nucleotide in said common position, the nucleotides of said flanking region which are not in said common position being randomized;
(b) assaying each of the sets for activity against the target molecule;
(c) selecting the set having the highest activity;
(d) preparing a further group of sets of oligonucleotides of said substantially same length, each of the sets of said further group having in the previously defined common position the nucleotide appearing in that position in the set selected in step (c), each set of said further group of sets having a different nucleotide in an additional defined common position, the nucleotides in the positions of the oligonucleotides which are not in a defined position being randomized;
(e) assaying each of the sets of said further group for said assayable activity;
(f) selecting the set of said further group having the highest activity;
(g) repeating steps (d) through (f) until an oligonucleotide having said assayable activity for said target molecule is determined.

32. The method of claim 31 wherein said oligonucleotide is a cyclic oligonucleotide.

33. The method of claim 31 wherein said cassette is prepared by a method comprising the steps of:
(a) preparing a group of sets of oligonucleotides of substantially the same length, each oligonucleotide comprising at least three nucleotides, by:
(i) defining a common position in the oligonucleotides of the sets, and
(ii) synthesizing said sets of oligonucleotides such that each set has a different nucleotide in said common position, the nucleotides which are not in said common position being randomized;
(b) assaying each of the sets for activity against the target molecule;
(c) selecting the set having the highest activity;
(d) preparing a further group of sets of oligonucleotides of said substantially same length, each of the sets of said further group having in the previously defined common position the nucleotide appearing in that position in the set selected in step (c), each set of said further group of sets having a different nucleotide in an additional defined common position, the nucleotides in the positions of the oligonucleotides which are not in a defined common position being randomized;
(e) assaying each of the sets of said further group for specific activity for the target molecule;
(f) selecting the set of said further group having the highest activity; and
(g) repeating steps (d) through (f) until an oligonucleotide cassette having said assayable activity for said target molecule is determined.

34. A method of determining an optimal set of monomers for oligomers having an assayable activity for a target molecule comprising:
(a) preparing a group of sets of oligomers of substantially the same length, each oligomer comprising at least three monomer units, by:
(i) selecting a group of monomer units, and
(ii) synthesizing sets of randomized oligomers, each set of randomized oligomers using all but at least one defined monomer unit from said group of monomer units, said excluded monomer unit being different for each set of oligomers;
(b) assaying each of the sets for activity against the target molecule;
(c) identifying each set of oligomers which expresses little or no activity against the target molecule;
(d) selecting monomers for inclusion in said optimal set wherein each defined monomer unit excluded from the sets identified in step (c) are selected.

35. The method of claim 34 wherein said oligomer has an ethylene glycol phosphate (egp) backbone.

36. The method of claim 34 wherein said oligomer has a hydroxy pyrrolidine phosphate (hpp) backbone.

37. The method of claim 34 wherein said oligomer is an oligonucleotide.

38. The method of claim 34 wherein said oligomer is a cyclic oligomer.

39. The method of claim 38 wherein said cyclic oligomer is a cyclic oligonucleotide.

40. The method of claim 38 wherein said cyclic oligomer is a cyclic amine.

41. A method for determining an oligonucleotide having an assayable activity for a non-antibody target molecule comprising the steps of:
(a) preparing a group of sets of oligonucleotides of substantially the same length, each oligonucleotide comprising at least three nucleotides, by:
(i) defining a common position in the oligonucleotides of the sets, and
(ii) synthesizing said sets of oligonucleotides such that each set has a different nucleotide in said common position, the nucleotides which are not in said common position being randomized;

(b) assaying each of the sets for activity against the target molecule;

(c) selecting the set having the highest activity;

(d) preparing a further group of sets of oligonucleotides of said substantially same length, each of the sets of said further group having in the previously defined common position the nucleotide appearing in that position in the set selected in step (c), and having in an additional defined common position a different nucleotide, the nucleotides in the positions of the oligonucleotides which are not in a defined common position being randomized;

(e) assaying each of the sets of said further group for said assayable activity;

(f) selecting the set of said further group having the highest assayable activity; and (g) repeating steps (d) through (f) until an oligonucleotide having said assayable activity for said target molecule is determined.

42. The method of claim 41 further comprising the steps of:

(h) selecting an oligonucleotide of step (g) with the highest assayable activity;

(i) preparing additional oligonucleotides, each additional oligonucleotide differing from the oligonucleotide of step (h) by at least one oligonucleotide which has been added, deleted, or substituted with a different nucleotide;

(j) assaying said additional oligonucleotides for said assayable activity; and (k) selecting the oligonucleotide of said additional oligonucleotides having the highest assayable activity.

43. The method of claim 42 wherein steps (i) through (k) are performed iteratively until no additional oligonucleotide having an increase in said assayable activity is identified.

44. The method of claim 42 wherein said oligonucleotide is a cyclic oligonucleotide.

45. The method of claim 41 wherein said oligonucleotide is from 3 to 20 nucleotides in length.

46. The method of claim 41 wherein said oligonucleotide is labeled with a detectable label.

47. The method of claim 41 wherein said assaying is by gel shift assay, streptavidin capture of biotinylated target, filter binding assay or affinity chromatography.

48. The method of claim 41 wherein the oligonucleotide is sterically constrained.

49. The method of claim 41 wherein said assayable activity is binding activity for a target molecule.

50. The method of claim 49 wherein the target molecule is a nucleic acid.

51. The method of claim 49 wherein said target molecule is a carbohydrate.

52. The method of claim 49 wherein said target molecule is a protein.

53. The method of claim 49 wherein said target molecule is a glycoprotein.

54. The method of claim 49 wherein the target molecule is a receptor, receptor binding ligand, antigen, enzyme, or transcription factor.

55. The method of claim 49 wherein the target molecule is a phospholipase, tumor necrosis factor, endotoxin, interleukin, leukotriene, plasminogen activator, protein kinase, cell adhesion molecule, lipoxygenase, hydrolase, transacylase, or transcription factor.

56. The method of claim 49 wherein the target molecule is derived from Candida, papilloma virus, Epstein-Barr virus, rhinovirus, hepatitis virus, human immunodeficiency virus, herpes simplex virus, influenza virus or cytomegalovirus.

57. The method of claim 49 wherein the target molecule is an RNA molecule or fragment thereof.

58. The method of claim 56 wherein the target molecule is the TAR element of human immunodeficiency virus.

59. The method of claim 56 wherein the target molecule is the gag-pol stem loop of human immunodeficiency virus.

60. The method of claim 56 wherein the target molecule is the 47-base pair stem loop of ras.

61. The method of claim 55 wherein the target molecule is endothelin-1.

62. The method of claim 55 wherein the target molecule is leukotriene B-4.

63. The method of claim 56 wherein the target molecule is human immunodeficiency virus gp120.

64. The method of claim 56 wherein the target molecule is human immunodeficiency virus tat protein.

65. The method of claim 41 wherein the assayable activity is catalytic activity.

66. The method of claim 41 wherein the assayable activity is induction of cellular production of interferon.

67. A method for determining an oligonucleotide having an assayable activity for a non-antibody target molecule comprising the steps of:

(a) binding a group of target molecules to a solid support;

(b) incubating the solid support with a group of oligonucleotides labeled with a detectable label having all positions randomized, under binding conditions;

(c) detecting the presence or absence of binding wherein binding of an oligonucleotide indicates activity of the oligonucleotide for one or more target molecules, thereby identifying selected target molecules;

(d) preparing a group of sets of oligonucleotides of substantially the same length, each oligonucleotide comprising at least three nucleotides, by:
  (i) defining a common position in the oligonucleotides of the sets, and
  (ii) synthesizing said sets of oligonucleotides such that each set has a different nucleotide in said common position, the nucleotides which are not in said common position being randomized;

(e) assaying each of the sets for activity against said target molecules;

(f) selecting the set having the highest activity;

(g) preparing a further group of sets of oligonucleotides of said substantially same length, each of the sets of said further group having in the previously defined common position the nucleotide appearing in that position in the set selected in step (f), and having in an additional defined common position a different nucleotide, the nucleotides in the positions of the oligonucleotides which are not in a defined common position being randomized;

(h) assaying each of the sets of said further group for said assayable activity for said selected target molecules;

(i) selecting the set of said further group having the highest activity; and (j) repeating steps (g) through (i) until an oligonucleotide having said assayable activity for a target molecule is determined.

68. The method of claim 67 wherein said oligonucleotide is a cyclic oligonucleotide.

69. A method for determining an oligonucleotide cassette having an assayable activity for a non-antibody target molecule comprising the steps of:

(a) preparing a group of sets of oligonucleotides of substantially the same length, each oligonucleotide comprising at least three nucleotides, by:
 (i) defining a common position in the oligonucleotides of the sets, and
 (ii) synthesizing said sets of oligonucleotides such that each set has a different nucleotide in said common position, the nucleotides which are not in said common position being randomized;
(b) assaying each of the sets for activity against the target molecule;
(c) selecting the set having the highest activity;
(d) preparing a further group of sets of oligonucleotides of said substantially same length, each of the sets having in the previously defined common position the nucleotide appearing in that position in the set selected in step (c), each set of said further group of sets having a different nucleotide in an additional defined common position, the nucleotides in the positions of the oligonucleotides which are not in a defined common position being randomized;
(e) assaying each of the sets of said further group for assayable activity for the target molecule;
(f) selecting the set of said further group having the highest activity; and
(g) repeating steps (d) through (f) until an oligonucleotide cassette having said assayable activity for said target molecule is determined.

70. The method of claim 69 wherein said oligonucleotide is a cyclic oligonucleotide.

71. A method for determining an oligonucleotide having an assayable activity for a non-antibody target molecule comprising the steps of:
 (a) preparing a group of sets of oligonucleotides of substantially the same length, each oligonucleotide comprising at least one predefined oligonucleotide cassette and at least one flanking region by:
  (i) defining a common position in said flanking region of the oligonucleotides of the sets, and
  (ii) synthesizing said sets of oligonucleotides such that each set has a different nucleotide in said common position, the nucleotides of said flanking region which are not in said common position being randomized;
 (b) assaying each of the sets for activity against the target molecule;
 (c) selecting the set having the highest activity;
 (d) preparing a further group of sets of oligonucleotides of said substantially same length, each of the sets of said further group having in the previously defined common position the nucleotide appearing in that position in the set selected in step (c), each set of said further group of sets having a different nucleotide in an additional defined common position, the nucleotides in the positions of the oligonucleotides which are not in a defined position being randomized;
 (e) assaying each of the sets of said further group for said assayable activity;
 (f) selecting the set of said further group having the highest activity; and
 (g) repeating steps (d) through (f) until an oligonucleotide having said assayable activity for said target molecule is determined.

72. The method of claim 71 wherein said oligonucleotide is a cyclic oligonucleotide.

73. The method of claim 71 wherein said cassette is prepared by a method comprising the steps of:
 (a) preparing a group of sets of oligonucleotides of substantially the same length, each oligonucleotide comprising at least three nucleotides, by:
  (i) defining a common position in the oligonucleotides of the sets, and
  (ii) synthesizing said sets of oligonucleotides such that each set has a different nucleotide in said common position, the nucleotides which are not in said common position being randomized;
 (b) assaying each of the sets for activity against the target molecule;
 (c) selecting the set having the highest activity;
 (d) preparing a further group of sets of oligonucleotides of said substantially same length, each of sets of said further group having in the previously defined common position the nucleotide appearing in that position in the set selected in step (c), each set of said further group of sets having a different nucleotide in an additional defined common position, the nucleotides in the positions of the oligonucleotides which are not in a defined, common position being randomized;
 (e) assaying each of the sets of said further group for specific activity for the target molecule;
 (f) selecting the set of said further group having the highest activity; and
 (g) repeating steps (d) through (f) until an oligonucleotide cassette having said assayable activity for said target molecule is determined.

74. A method of determining an optimal set of monomers for oligomers having an assayable activity for a non-antibody target molecule comprising:
 (a) preparing a group of sets of oligomers of substantially the same length, each oligomer comprising at least three monomer units, by:
  (i) selecting a group of monomer units, and
  (ii) synthesizing sets of randomized oligomers, each set of randomized oligomers using all but at least one defined monomer unit from said group of monomer units, said excluded monomer unit being different for each set of oligomers;
 (b) assaying each of the sets for activity against the target molecule;
 (c) identifying each set of oligomers which expresses little or no activity against the target molecule;
 (d) selecting monomers for inclusion in said optimal set wherein each defined monomer unit excluded from the sets identified in step (c) are selected.

75. The method of claim 74 wherein said oligomer has an ethylene glycol phosphate (egp) backbone.

76. The method of claim 74 wherein said oligomer has a hydroxy pyrrolidine phosphate (hpp) backbone.

77. The method of claim 74 wherein said oligomer is an oligonucleotide.

78. The method of claim 74 wherein said oligomer is a cyclic oligomer.

79. The method of claim 78 wherein said cyclic oligomer is a cyclic oligonucleotide.

80. The method of claim 78 wherein said cyclic oligomer is a cyclic amine.

* * * * *

UNITED STATES PATENT AND TRADEMARK OFFICE
CERTIFICATE OF CORRECTION

PATENT NO. : 5,698,391
DATED : December 16, 1997
INVENTOR(S) : Cook et al.

It is certified that error appears in the above-identified patent and that said Letters Patent is hereby corrected as shown below:

Col. 21, line 13, please delete "conected" and insert therefor --connected--.
Col. 28, line 19, please delete "transcriptass" and insert therefor --transcriptase--.
Col. 40, line 25, please delete second occurrence of the word "with".

Signed and Sealed this

Nineteenth Day of January, 1999

Attest:

Attesting Officer

*Acting Commissioner of Patents and Trademarks*